United States Patent
Chapman et al.

(10) Patent No.: US 9,857,333 B2
(45) Date of Patent: Jan. 2, 2018

(54) PENS FOR BIOLOGICAL MICRO-OBJECTS

(71) Applicant: Berkeley Lights, Inc., Emeryville, CA (US)

(72) Inventors: Kevin T. Chapman, Santa Monica, CA (US); Igor Y. Khandros, Orinda, CA (US); Gaetan L. Mathieu, Vareenes (CA); J. Tanner Nevill, El Cerrito, CA (US); Ming C. Wu, Moraga, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 988 days.

(21) Appl. No.: 14/060,117

(22) Filed: Oct. 22, 2013

(65) Prior Publication Data
US 2014/0116881 A1 May 1, 2014

Related U.S. Application Data

(60) Provisional application No. 61/720,956, filed on Oct. 31, 2012.

(51) Int. Cl.
| | |
|---|---|
| *B01L 3/00* | (2006.01) |
| *G01N 27/447* | (2006.01) |
| *G01N 27/26* | (2006.01) |
| *B03C 5/00* | (2006.01) |
| *B03C 5/02* | (2006.01) |

(52) U.S. Cl.
CPC .. *G01N 27/44791* (2013.01); *B01L 3/502761* (2013.01); *B03C 5/005* (2013.01); *B03C 5/026* (2013.01); *B01L 2200/0668* (2013.01); *B01L 2300/0816* (2013.01); *B01L 2300/0819* (2013.01); *B01L 2300/0877* (2013.01); *B01L 2400/0424* (2013.01);

(Continued)

(58) Field of Classification Search
CPC .. B01L 3/502761; B01L 3/5027; B01L 3/502; B01L 3/50; G01N 27/447; G01N 27/416; G01N 27/26
USPC ......... 204/451, 601; 422/50, 68.1, 500, 527, 422/547; 436/180
See application file for complete search history.

(56) References Cited

U.S. PATENT DOCUMENTS

| | | |
|---|---|---|
| 6,294,063 B1 | 9/2001 | Becker et al. |
| 6,942,776 B2 | 9/2005 | Medoro |

(Continued)

FOREIGN PATENT DOCUMENTS

| | | |
|---|---|---|
| EP | 1065378 A2 | 1/2001 |
| JP | 2005-521425 | 7/2005 |

(Continued)

OTHER PUBLICATIONS

Jen et al., "Single-Cell Chemical Lysis on Microfluidic Chips with Arrays of Microwells," Sensors 2012(12)347-358 (Dec. 30, 2011).

(Continued)

*Primary Examiner* — Christine T Mui
(74) *Attorney, Agent, or Firm* — Kenneth E. Horton; Kirton McConkie

(57) ABSTRACT

Individual biological micro-objects can be deterministically selected and moved into holding pens in a micro-fluidic device. A flow of a first liquid medium can be provided to the pens. Physical pens can be structured to impede a direct flow of the first medium into a second medium in the pens while allowing diffusive mixing of the first medium and the second medium. Virtual pens can allow a common flow of medium to multiple ones of the pens.

41 Claims, 15 Drawing Sheets

(52) U.S. Cl.
CPC . *B01L 2400/0454* (2013.01); *B01L 2400/086* (2013.01); *B03C 2201/26* (2013.01)

(56) References Cited

U.S. PATENT DOCUMENTS

| | | | |
|---|---|---|---|
| 6,958,132 B2 | 10/2005 | Chiou et al. |
| 7,090,759 B1 | 8/2006 | Seul |
| 7,612,355 B2 | 11/2009 | Wu et al. |
| 7,956,339 B2 | 6/2011 | Ohta et al. |
| 2003/0008364 A1 | 1/2003 | Wang et al. |
| 2004/0072278 A1 | 4/2004 | Chou |
| 2004/0191789 A1 | 9/2004 | Manaresi et al. |
| 2004/0197905 A1 | 10/2004 | Hafeman |
| 2005/0112548 A1 | 5/2005 | Segawa |
| 2005/0175981 A1 | 8/2005 | Voldman |
| 2006/0091015 A1 | 5/2006 | Lau |
| 2006/0154361 A1 | 7/2006 | Wikswo et al. |
| 2007/0095669 A1 | 5/2007 | Lau |
| 2007/0183934 A1 | 8/2007 | Diercks et al. |
| 2008/0085556 A1 | 4/2008 | Graefing |
| 2008/0223721 A1 | 9/2008 | Cohen et al. |
| 2008/0257735 A1 | 10/2008 | Jeon et al. |
| 2008/0302732 A1 | 12/2008 | Soh |
| 2009/0023608 A1 | 1/2009 | Hung |
| 2010/0003666 A1 | 1/2010 | Lee et al. |
| 2010/0273681 A1 | 10/2010 | Cerrina et al. |
| 2011/0117634 A1 | 5/2011 | Halamish et al. |
| 2011/0262906 A1 | 10/2011 | Dimov |
| 2012/0024708 A1 | 2/2012 | Chiou et al. |
| 2012/0118740 A1 | 5/2012 | Carcia et al. |
| 2012/0325665 A1 | 12/2012 | Chiou et al. |
| 2013/0171628 A1 | 7/2013 | Di Carlo et al. |
| 2013/0190212 A1 | 7/2013 | Handique et al. |
| 2013/0252258 A1 | 9/2013 | Bocchi et al. |
| 2016/0252495 A1 | 9/2016 | Ricicova et al. |

FOREIGN PATENT DOCUMENTS

| | | |
|---|---|---|
| WO | 2004089810 A2 | 10/2004 |
| WO | 2009053907 | 4/2009 |
| WO | 2009146143 | 12/2009 |
| WO | 201014078 | 12/2010 |
| WO | 2011149032 A1 | 12/2011 |
| WO | 2011160430 A1 | 12/2011 |
| WO | 2013148745 | 10/2013 |

OTHER PUBLICATIONS

Young et al., Fundamentals of Microfluidic Cell Culture in Controlled Microenvironments, Chem Soc Rev 39 (3):1036-48 (2010).

Han et al., Integration of Single Oocyte Trapping, In Vitro Fertilization and Embryo Culture in a Microwell-Structured Microfluidic Device, Lab on a Chip 10:2848-54 (2010).

European Patent Office, Supplementary Search Report, Application Serial No. 13850976.5 , dated Jun. 24, 2016 (7 pages).

Carlo et al., "Dynamic Single Cell Analysis for Quantitative Biology," Analytical Chemistry (Dec. 1, 2006), pp. 7918-7925.

Ryan et al., "Single Cell Cloning by Serial Dilution," Corning Life Sciences (May 2005), pp. 1-3.

International Preliminary Report on Patentability, PCT Application Serial No. PCT/US2013/067479 (May 5, 2015), 9 pages.

Chiou et al., "Massively parallel manipulation of single cells and microparticles using optical images," Nature, vol. 436 (Jul. 21, 2005), pp. 370-372.

Dishinger et al., "Serial Immunoassays in Parallel on a Microfluidic Chip for Monitoring Hormone Secretion from Living Cells," Analytical Chemistry vol. 79, No. 3 (Feb. 1, 2007), pp. 947-954.

The International Search Report and the Written Opinion of the International Searching Authority, PCT Application Serial No. PCT/US2013/067479 (dated Feb. 5, 2014), 13 pages.

Valley et al., "Optoelectronic Tweezers as a Tool for Parallel Single-Cell Manipulation and Simulation," IEEE Transactions on Biomedical Circuits and Systems, vol. 3, No. 6 (Dec. 2009), pp. 424-431.

Yi et al., "Microfluidics technology for manipulation and analysis of biological cells," Analytica Chimica Acta 560 (2006), pp. 1-23.

Chiou, Pei-Yu, Massively Parallel Optical Manipulation of Cells, Micro- and Nano-Particles on Optoelectronic devices, Dissertation, University of California at Berkeley, 2005 (147 pages).

Iliescu et al., Continuous Field-FLow Separation of Particle Populations in a Dielectrophoretic Chip with Three Dimensional Electrodes, Applied Physics Letters 90:234104 (2007).

Nevill et al., Integrated Microfluidic Cell Culture and Lysis on a Chip, Lab on a Chip 7:1689-95 (2007).

Lee et al., Microfluidic Chemostat and Turbidostat with Flow Rate, Oxygen and Temperature Control for Dynamic Continuous Culture , Lab on a Chip 11:1730-39 (2011).

Hur et al., High-throughput Size-Based Rare Cell Enrichment Using Microscale Vortices, Biomicrofluidics 5:022206 (2011).

Chung et al., Imaging Single-Cell Signaling Dynamics with a Deterministic High-Density Single-Cell Trap Array, Anal. Chem. 83(18):7044-7052 (2011).

Chen et al., Microfluidic Approaches for Cancer Cell Detection, Characterization, and Separation, Lab on a Chip 12:1753 (2012).

Japanese Patent Office, Notice of Reasons for Rejection for Application No. 2015-539940, dated Sep. 19, 2017.

Somaweera H. et al., Generation of a Chemical Gradient Across an Array of 256 Cell Cultures in a Single Chip. Analyst, Oct. 7, 2013, vol. 138, No. 19, pp. 5566-5571.

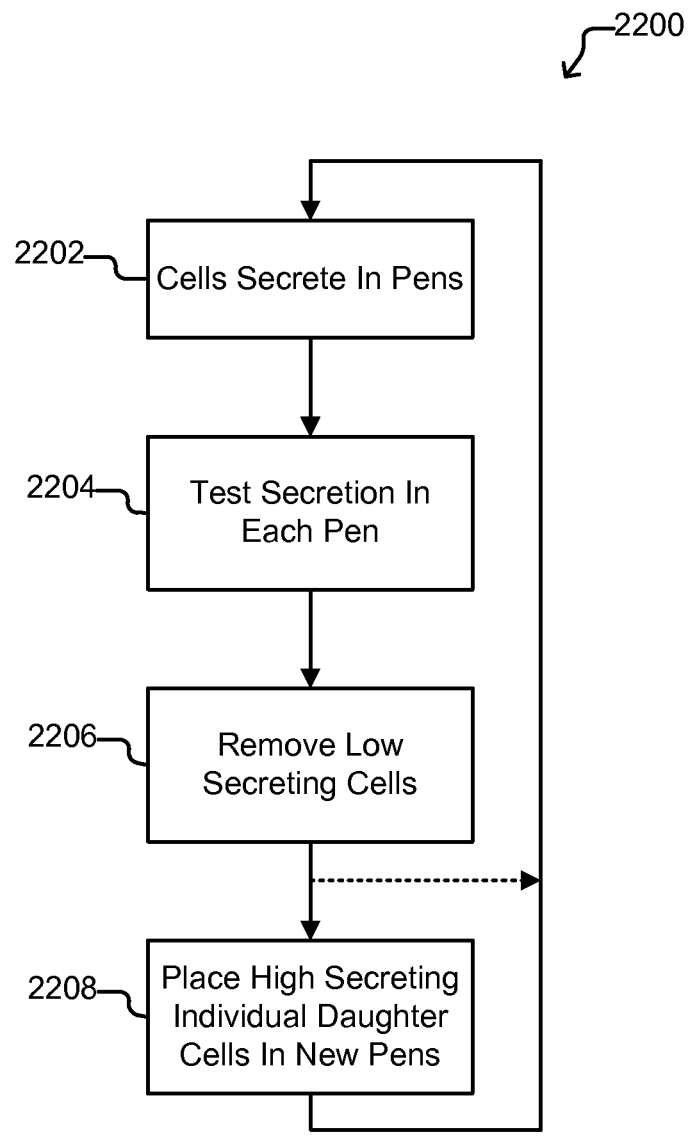

PENS FOR BIOLOGICAL MICRO-OBJECTS

CROSS REFERENCE TO RELATED APPLICATION(S)

This application is a non-provisional (and thus claims the benefit) of U.S. provisional patent application Ser. No. 61/720,956 (filed Oct. 31, 2012), which is incorporated by reference herein in its entirety.

BACKGROUND

In bioscience fields, activities of biological micro-objects such as cells are often studied and analyzed. For example, cells that produce at least a minimum number of clones or secrete desired materials can be utilized in the production of medicines or in the study of diseases. It can thus be advantageous to identify cells that produce clones at or above a minimum rate or that secrete certain materials. Embodiments of the present invention are directed to improved micro-fluidic devices and processes for placing selected biological micro-objects into holding pens, conditioning the micro-objects in the pens, monitoring biological activity of the micro-objects in the pens, and/or moving the micro-objects whose biological activity meets a predetermined threshold from the pens for further use or processing.

SUMMARY

In some embodiments, a method of processing biological micro-objects can include actively placing individual biological micro-objects in interior spaces of holding pens in a micro-fluidic device and providing a flow of a first liquid medium to the pens over a time period. The method can also include, while providing the flow, impeding direct flow of the first medium from the flow into the interior spaces of the holding pens.

In some embodiments, a micro-fluidic apparatus can include a housing and holding pens. The housing can be disposed on a base, and the housing can include a flow path for a first liquid medium. The holding pens can be disposed within the housing, and each pen can comprise an enclosure enclosing an interior space. The enclosure can be structured to hold a biological micro-object suspended in a second liquid medium and impede a direct flow of the first medium into the second medium in the interior space.

A method of processing biological micro-objects can include creating virtual holding pens in a micro-fluidic device by directing a pattern of light in the form of the holding pens into the micro-fluidic device and thereby activating dielectrophoresis (DEP) electrodes. The method can also include placing individual biological micro-objects into the holding pens, where each of the holding pens isolates any one or more of the individual micro-objects in the holding pen from all of the micro-objects outside of the holding pen. The method can also include providing the micro-objects in the holding pens with a common flow of a liquid medium over a time period.

BRIEF DESCRIPTION OF THE DRAWINGS

FIG. 22 illustrates a process showing another example of operation of the device of FIG. 1A configured with the OET device of FIG. 2 according to some embodiments of the invention.

DETAILED DESCRIPTION OF EXEMPLARY EMBODIMENTS

Figure 1A:
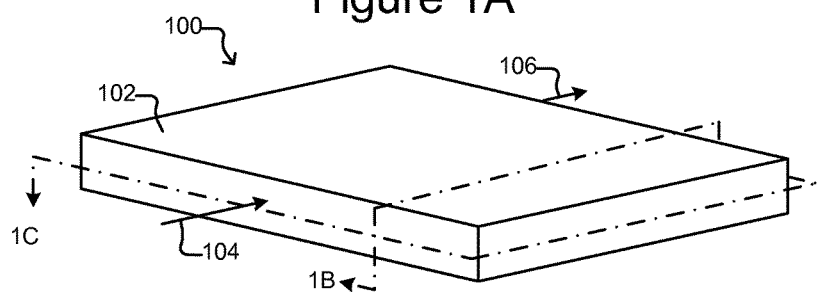
FIG. 1A illustrates an example of a micro-fluidic device according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the Figures may show simplified or partial views, and the dimensions of elements in the Figures may be exaggerated or otherwise not in proportion for clarity. In addition, as the terms "on," "attached to," or "coupled to" are used herein, one element (e.g., a material, a layer, a substrate, etc.) can be "on," "attached to," or "coupled to" another element regardless of whether the one element is directly on, attached, or coupled to the other element or there are one or more intervening elements between the one element and the other element. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

The words "substantially" and "generally" mean sufficient to work for the intended purpose. The term "ones" means more than one.

The term "cell" refers to a biological cell. The term "clones," with reference to cells, means cells that are identical because each cell was grown from the same parent cell. Clones are thus all "daughter cells" of the same parent cell.

As used herein, the term "biological micro-object" includes biological cells and compounds such as proteins, embryos, plasmids, oocytes, sperms, genetic material (e.g., DNA), transfection vectors, hydridomas, transfected cells, and the like as well as combinations of the foregoing.

As used herein a dielectrophoresis (DEP) electrode refers to a terminal on or a region of an inner surface of a chamber for containing a liquid medium at which DEP forces in the medium sufficient to attract or repel micro-objects in the medium can be selectively activated and deactivated.

The term "flow," as used herein with reference to a liquid or gas, includes without limitation a continuous, pulsed, periodic, random, intermittent, or reciprocating flow of the liquid or gas. A "convection flow" is a flow of a liquid or gas that is driven by pressure. A "diffusive flow" or "diffusion" is a flow of liquid or gas that is driven by random thermal motion. The term "diffusive mixing" as used with respect to two or more liquid or gas media means the mixing of the media due to spontaneous intermingling of the media as a result of random thermal motion. The term "substantially," as used herein with respect to "convection flow," diffusive flow," "diffusion," or "diffusive mixing," means more than fifty percent.

The term "deterministic," when used to describe selecting or placing a micro-object, means selecting or placing a specifically identified and desired micro-object from a group of micro-objects. Deterministically selecting or placing a micro-object thus does not include randomly selecting or placing merely any one of the micro-objects in a group or sub-group of micro-objects.

As used herein, the meaning of the term "processing" a micro-object includes any one or more of the following: moving (e.g., in a flow of liquid medium, with an OET device, or the like), sorting, and/or selecting one or more of the micro-objects; modifying one or more of the micro-objects, wherein examples of such modifying include growing populations of micro-objects that are cells or other living biological entities, fusing two or more such micro-objects together, and transfecting one or more micro-objects; monitoring micro-objects; monitoring growth, secretions, or the like of micro-objects that are cells or other living biological entities; and/or conditioning micro-objects that are cells or other living biological entities.

Embodiments of the invention include deterministically placing individual biological micro-objects in holding pens in a micro-fluidic device. A flow of a first liquid medium can be provided to the pens, but the pens can be structured to impede a direct flow of the first medium into a second medium in the pens while allowing diffusive mixing of the first medium in the flow and the second medium in the pens.

Figure 1B:
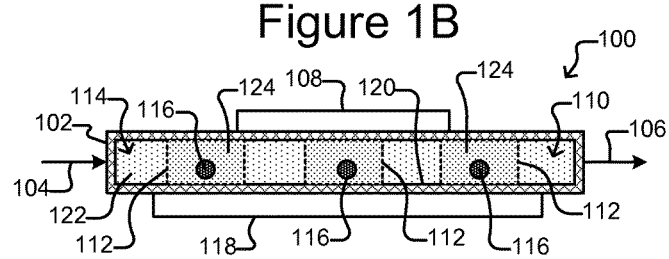
FIG. 1B is a side, cross-sectional view of the device of FIG. 1A.
Figure 1C:
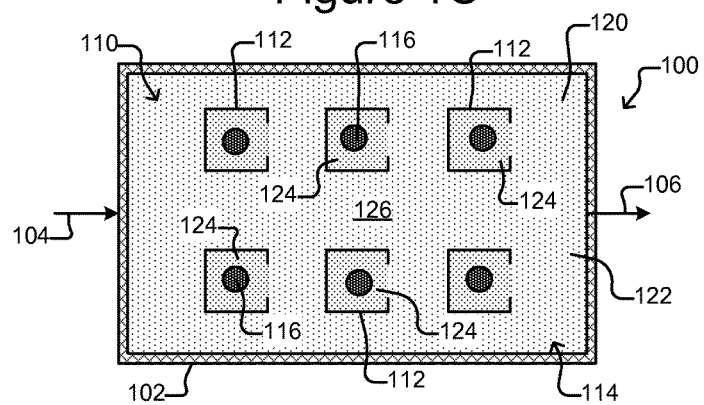
FIG. 1C is a top, cross-sectional view of the device of FIG. 1A.

FIGS. 1A-1C illustrate an example of a micro-fluidic device 100 according to some embodiments of the invention. As shown, the micro-fluidic device 100 can comprise a housing 102, an electrode mechanism 108, and a monitoring mechanism 118. As also shown, the housing 102 can comprise an interior chamber 110 for holding one or more liquid media 114 in which a plurality of biological micro-objects 116 can be suspended. The media 114 can be disposed on an inner surface 120 of the chamber 110. A plurality of holding pens 112 for the micro-objects 116 can be disposed in the chamber 110. As will be seen, each pen 112 can be a virtual pen, a physical pen, and/or a combination virtual/physical pen.

The media 114 in the device 100 can comprise, for example, a first medium 122 and a second medium 124. The first medium 122 can be media 114 that is in the flow path 126, and the second medium 124 can be media 114 that is inside the holding pens 112. The first medium 122 can be the same type of medium as the second medium 124. Alternatively, the first medium 122 can be a different type of medium than the second medium 124.

The housing 102 can comprise an enclosure that defines the chamber 110. As shown, the housing 102 can also comprise one or more inlets 104 through which media 114 and micro-objects 116 can be input into the chamber 110. There can be one or more flow paths 126 in the chamber 110 for the media 114. For example, as illustrated in FIG. 1C, the chamber 110 can comprise a flow path 126 for media 114 from the inlet 104 to the outlet 106.

An inlet 104 can be, for example, an input port, an opening, a valve, a channel, or the like. The housing 102 can also comprise one or more outlets 106 through which media 114 and micro-objects 116 can be removed. Micro-objects 116 can alternatively be removed from the housing 102 in other ways. For example, as noted below, a needle-like aspirator (not shown) can pierce the housing 102, and one or more micro-objects 116 can be removed with the aspirator. An outlet 106 can be, for example, an output port, an opening, a valve, a channel, or the like. As another example, the outlet 106 can comprise a droplet outputting mechanism such as any of the outputting mechanisms disclosed in U.S. patent application Ser. No. 13/856,781 filed Apr. 4, 2013. All or part of the housing 102 can be gas permeable to allow gas (e.g., ambient air) to enter and exit the chamber 110, for example, to sustain the biological micro-objects 116 in the chamber 110. For example, a flow of gas can be applied to the gas permeable portion of the housing 102. For example, a pulsed, regulated, or otherwise controlled flow of gas can be applied as needed (e.g., when testing indicates that micro-objects (e.g., cells) in the housing 102 need gas).

Although not shown, the device 100 can comprise sensors or similar components that detect relevant conditions of media 114 or the chamber 110 such as temperature, the chemical composition of media 114 (e.g., the level of dissolved oxygen, carbon dioxide, or the like in media 114), the pH of media 114, osmolarity of media 114, or the like. The housing 102, for example, can comprise such sensors or components, which can be configured with a controller (not shown) to control input of media 114 through the inlet 104 to maintain constant or controllably adjust certain conditions (such as the conditions identified above) of media 114.

The electrode mechanism 108 (shown in FIG. 1B) can be configured to create selectively electrokinetic forces on micro-objects 116 in media 114. For example, the electrode mechanism 108 can be configured to selectively activate (e.g., turn on) and deactivate (e.g., turn off) dielectrophoresis (DEP) electrodes at the inner surface 120 of the chamber 110 on which media 114 is disposed. The DEP electrodes can create forces in media 114 that attract or repel micro-objects 116, and the electrode mechanism 108 can thus select and/or move one or more of the micro-objects 116 in media 114. For example, in some embodiments, the electrode mechanism 108 can be configured such that hardwired electrical connections to the DEP electrodes at the inner surface 120 can activate and deactivate the individual DEP electrodes. In other embodiments, the individual DEP electrodes at the inner surface 120 can be optically controlled. An example comprising an optoelectronic tweezers mechanism is illustrated in FIG. 2 and discussed below.

For example, the electrode mechanism 108 can include one or more optical (e.g., laser) tweezers devices and/or one or more optoelectronic tweezers (OET) devices (e.g., as disclosed in U.S. Pat. No. 7,612,355, which is incorporated in its entirety by reference herein). As yet another example, the electrode mechanism 108 can include one or more devices (not shown) for moving a droplet of media 114 in which one or more of the micro-objects 116 are suspended. Such devices (not shown) can include electrowetting devices such as optoelectronic wetting (OEW) devices (e.g., as disclosed in U.S. Pat. No. 6,958,132). The electrode mechanism 108 can thus be characterized as a DEP device in some embodiments.

The monitoring mechanism 118 can comprise any mechanism for observing, identifying, or detecting individual micro-objects 116 in media 114. In some embodiments, the monitoring mechanism 118 can also comprise a mechanism for monitoring biological activity or a biological state of micro-objects 116 in the pens 112.

Figure 2:
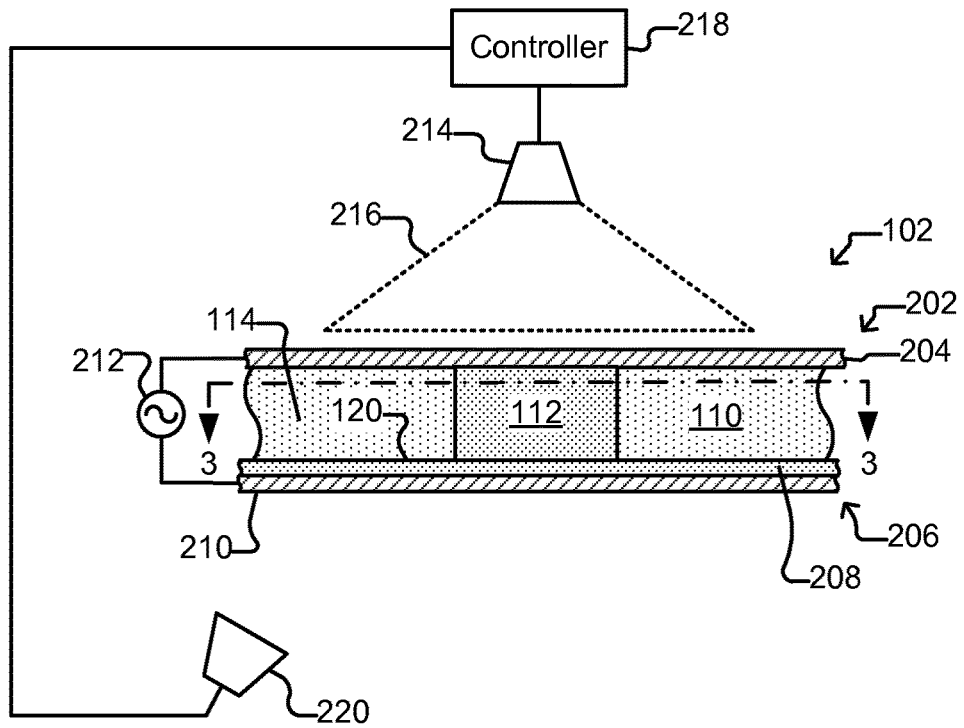
FIG. 2 shows a cross-sectional side view of the device of FIG. 1A illustrating an example of the device configured with an optoelectronic tweezers (OET) device according to some embodiments of the invention.

As shown in FIG. 2, the monitoring mechanism 118 can comprise an imaging device 220. For example, the imaging device 220 can comprise a camera or similar device for capturing images of micro-objects 116 in the chamber 110, including in the pens 112. As also shown, a controller 218 can control the imaging device 220 and process images captured by the imaging device 220. Although shown as disposed below the device 102 in FIG. 2, the imaging device 220 can be disposed in other locations such as above or to the side of the device 102.

As also shown in FIG. 2, the electrode mechanism 108 can comprise an OET device. For example, as shown, the electrode mechanism 108 can comprise a first electrode 204, a second electrode 210, an electrode activation substrate 208, and a power source 212. As shown, media 114 in the chamber 110 and the electrode activation substrate 208 can separate the electrodes 204, 210. A pattern of light 216 from the light source 214 can selectively activate a desired pattern of individual DEP electrodes at the inner surface 120 of the chamber 110. That is, light in the light pattern 216 can reduce the electrical impedance of the electrode activation substrate 208 at a pattern of small "electrode" regions of the inner surface 120 of the chamber 110 to less than the impedance of the media 114. The foregoing creates an electric field gradient in the media 114 from the electrode region of the surface 120 to the first electrode 204, which in turn creates local DEP forces that attract or repel nearby micro-objects 116. Different patterns of individual DEP electrodes that attract or repeal micro-objects 116 in media 114 can thus be selectively activated and deactivated at many different such electrode regions at the inner surface 120 of the chamber 110 by different light patterns 216 projected form a light source 214 (e.g., a laser source or other type of light source) into the micro-fluidic device 100.

In some embodiments, the electrode activation substrate 208 can be a photoconductive material, and the inner surface 120 can be featureless. In such embodiments, the DEP electrodes can be created anywhere and in any pattern on the inner surface 120 of the chamber 110 in accordance with the light pattern 126 (see FIG. 2). Examples are illustrated in the aforementioned U.S. Pat. No. 7,612,355 in which the undoped amorphous silicon material 24 shown in the drawings of the foregoing patent can be an example of photoconductive material that can compose the electrode activation substrate 208.

In other embodiments, the electrode activation substrate 208 can comprise a circuit substrate such as a semiconductor material comprising a plurality of doped layers, electrically insulating layers, and electrically conductive layers that form semiconductor integrated circuits such as known in semiconductor fields. In such embodiments, electric circuit elements can form electrical connections between electrode regions at the inner surface 120 of the chamber 110 and the second electrode 210 that can be selectively activated and deactivated by changing patterns of the light pattern 216. When not activated, each electrical connection can have high impedance such that the voltage drop from a corresponding electrode region at the inner surface 120 of the chamber 110 to the second electrode 210 is greater than the voltage drop from the first electrode 204 through media 114 to the corresponding electrode region. When activated by light in the light pattern 216, however, each electrical connection can have low impedance such that the voltage drop from a corresponding electrode region at the inner surface 120 of the chamber 110 to the second electrode 210 is less than the voltage drop from the first electrode 204 through media 114 to the corresponding electrode region, which activates a DEP electrode at the corresponding electrode region as discussed above. DEP electrodes that attract or repeal micro-objects 116 in media 114 can thus be selectively activated and deactivated at many different "electrode" regions at the inner surface 120 of the chamber 110 by the light pattern 216. Non-limiting examples of such configurations of the electrode activation substrate 208 include the phototransistor-based OET device 200 illustrated in FIGS. 21 and 22 of U.S. Pat. No. 7,956,339.

In some embodiments, the first electrode 204 can be part of an upper wall 202 of the housing 102, and the electrode activation substrate 208 and second electrode 210 can be part of a lower wall 206 of the housing 102 generally as illustrated in FIG. 2. As shown, the upper wall 202 and lower wall 206 can define the chamber 110, and media 114 can be disposed on the inner surface 120 of the chamber 110. The foregoing, however, is but an example. In other embodiments, the first electrode 204 can be part of the lower wall 206 and one or both of the electrode activation substrate 208 and/or second electrode 210 can be part of the upper wall 202. As another example, the first electrode 204 can be part of the same wall 202 or 206 as the electrode activation substrate 208 and the second electrode 210. For example, the electrode activation substrate 208 can comprise the first electrode 204 and/or the second electrode 210. Moreover, the light source 214 can alternatively be located below the housing 102, and/or the imaging device 220 and the light source 214 can alternatively be located on the same side of the housing 102.

As mentioned, in some embodiments of the invention, part or all of each pen 112 can be "virtual," which as used herein, means that part or all of the pen 112 comprises DEP forces from activated DEP electrodes at electrode regions of the interior surface 120 of the chamber 110 (as discussed above) rather than physical barriers.

Figure 3:
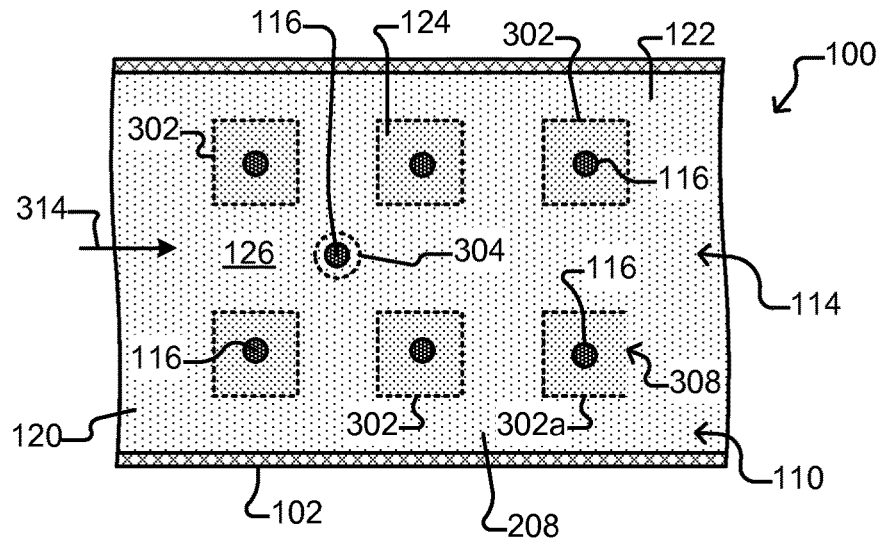
FIG. 3 is a top, cross-sectional partial view of the device of FIG. 1A configured with the OET device of FIG. 2 and virtual pens according to some embodiments of the invention.

FIG. 3 (which shows a partial, top cross-sectional view of part of the housing 102) illustrates an example of the device 100 of FIGS. 1A-1C in which the pens 112 (which are designated 302 in FIG. 3) are virtual pens 302 according to some embodiments of the invention. The virtual pens 302 in FIG. 3 can be created in the chamber 110 by the electrode mechanism 108 configured, for example, as the OET device of FIG. 2. That is, the virtual pens 302 can comprise a pattern of activated DEP electrodes at the inner surface 120 of the chamber 110. Although one micro-object 116 is shown in each pen 302, there can alternatively be more than one micro-object 116 in each pen.

As shown in FIG. 3, a flow 314 of media 114 through the chamber 110 can be provided in a flow path 126. As illustrated in FIG. 3, each pen 302 can isolate the micro-object(s) 116 in the pen 302 from the micro-objects 116 in the other pens 302. The flow 314 of media 114, however, can be a common flow 314 provided to some or all of the pens 302 and thus the micro-objects 116 in the pens 302. Configured as shown in FIG. 3, each pen 302 can thus isolate the micro-object(s) 116 inside the pen 302 from micro-objects 116 outside of the pen 302 including micro-objects 116 in other pens 302 and thus prevent a micro-object 116 from outside of a particular pen 302 from mixing with the micro-object(s) inside that particular pen 302 while allowing a common flow 314 of media 114 to flow into (by convection flow) and out of multiple pens 116 and thus, for example, supply nutrients and carry away waste from micro-objects 116 in multiple pens 116.

The virtual pens 302 can comprise light enclosures in the light pattern 216 projected by the light source 214 into the housing 102 of the micro-fluidic device 100 as shown in FIG. 2. The power source 212 of the OET of FIG. 2 can be configured with a frequency that causes the light enclosure that defines each pen 302 to repel a micro-object 116 so that each pen 302 holds a micro-object 116 inside the pen 302. Moreover, one or more of the virtual pens 302 can be moved, expanded or contracted, turned off, or the like by changing the light pattern 216 projected into the housing 102.

As shown in FIG. 3, the OET device depicted in FIG. 2 can also create a light trap 304 (e.g., cage) that traps a micro-object 116 to select and move the micro-object 116. The light trap 304 can be, for example, a light cage that traps the micro-object 116. The frequency of the power source 212 in FIG. 2 can be such that the light trap 304 repels the selected micro-object 116. The micro-object 116 can thus be moved in the chamber 110 by moving the light trap 304 on the electrode activation substrate 208. The detector 220 can capture images of the micro-objects 116 in the channel 110 (e.g., a flow path 126), which can be an example of a common space. Specific, desired individual ones of the micro-objects 116 can thus be identified and then selected with the selector 118 (e.g., configured as the OET device of FIG. 2), for example, with light traps 302, 412 as discussed below with respect to FIGS. 3 and 4. The detector 220 and selector 118 (e.g., configured as the OET device of FIG. 2) can thus be examples of a means for deterministically selecting or placing one or more of the micro-objects 116.

Although illustrated as squares in FIG. 3, the pens 302 can alternatively be other shapes. For example, the pens 302 can be circles, ovals, rectangles, triangles, or the like. Moreover, the pens 302 need not be fully enclosed. For example, any of the pens 302 can have an opening 308 as illustrated by pen 302a in FIG. 3. Although illustrated as a circle, the light trap 304 can be other shapes such as square, oval, rectangular, triangular, or the like. In addition, the pens 302 can be difference sizes and can be disposed in different orientations.

Figure 4:
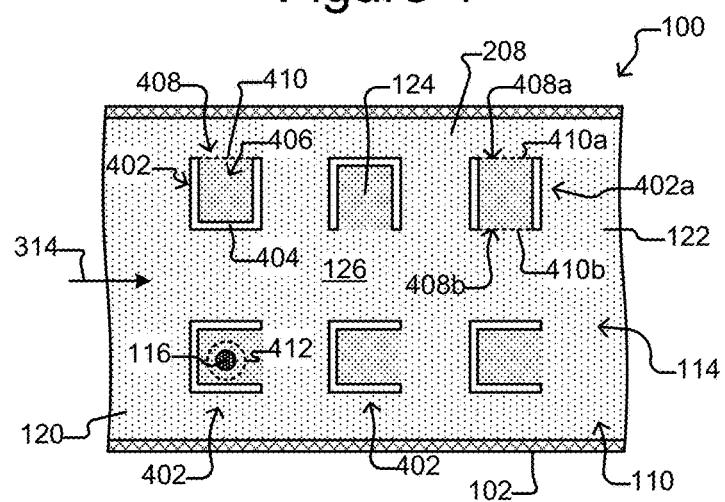
FIG. 4 is a top, cross-sectional partial view of the device of FIG. 1A configured with the OET device of FIG. 2 and pens that are physical and/or virtual according to some embodiments of the invention.

FIG. 4 (which shows a partial, top cross-sectional view of part of the housing 102) illustrates another example of a configuration of the device 100 of FIGS. 1A-1C. In the configuration illustrated in FIG. 4, the pens 112 (which are designated 402 in FIG. 4) can be entirely physical or both physical and virtual. For example, as shown, each pen 402 can comprise a physical barrier 404 (e.g., as part of the housing 102), which can define or be part of an enclosure 406 with an opening 408 that is in fluidic communication (e.g., contact) with a flow 314 of media 114 through the chamber 110.

Generally as discussed with respect to FIG. 3, a flow 314 of media 114 through the chamber 110 can be provided in a flow path 126. Each pen 402 can isolate the micro-object(s) 116 in the pen 402 from the micro-objects 116 in the other pens 302. For example, each pen 302 can prevent any micro-object 116 outside the pen 302 from mixing with any of the micro-objects inside the pen 302. The flow 314 of media 114, however, can be a common flow 314 provided to all of the pens 402 and thus all of the micro-objects 116 in the pens 402. The pens 402, however, can be structured so that the first medium 122 from the flow 314 does not flow directly into any of the pens 402, but the structure of the pens 402 can allow diffusive mixing of the first medium 122 from the flow 314 and the second medium 124 inside the pens 402.

For example, the barrier 404 of each pen 402 can be shaped and oriented to impede direct flow of the first medium 122 from the flow 314 in the flow path 126 into the pen 402. For example, each pen 402 can be shaped and oriented such that a portion of the physical barrier 404 directly faces the direction of the flow 314 but no opening (e.g., the opening 408) directly faces the direction of the flow 314. In the example illustrated in FIG. 3, each of the pens 402 thus impede direct flow of the first medium 122 from the flow 314 in the flow path 126 into the pen 402.

As another example, the barrier 404 can be shaped and oriented to prevent convection flow of the first medium 122 from the flow 314 in the flow path 126 into the pen 402. Each pen 402 can, however, be shaped and oriented to allow substantially only diffusion mixing of the first medium 122 from the flow 314 in the flow path 126 and the second medium 424 inside the pen 402. For example, each pen 402 can comprise an opening shaped and oriented to allow such diffusive mixing.

In some embodiments, however, the pens 402 can be oriented with the opening 408 pointed in any direction with respect to the flow 314 of media 114. As also shown, any of the pens 402 can comprise both a physical barrier and a virtual portion. For example, in some embodiments, a virtual door 410 comprising adjacent activated DEP electrodes on the inner surface 120 of the chamber 110 can be created and/or removed at the opening 408 of one or more of the physical barriers 404 to make the pen 402 selectively fully enclosed generally as shown in FIG. 4. The virtual door 410 can correspond to light in the light pattern 214 projected onto the electrode activation substrate 208. (See FIG. 2.)

As also illustrated in FIG. 4, one or more of the pens 402 can comprise more than one such virtual door 410. For example, as shown, pen 402a comprises more than one opening 408a, 408b into the pen 402a, and there can be a virtual door 410a, 410b at each such opening 408a, 408b. In operation, a micro-object 116 can be moved into the pen 402a through the first opening 408a while the first virtual door 410a is turned off, and the micro-object 116 can later be moved out of the pen 402a through the second opening 408b while the second virtual door 410b is turned off.

A light trap 412 (which can be similar to or the same as light trap 304) can be created on the surface 120 of the chamber 110 by the electrode mechanism 108 configured as the OET device of FIG. 2. The light trap 412 can be created that traps a micro-object 116 to select the micro-object 116. The frequency of the power source 212 in FIG. 2 can be such that the light trap 412 repels the selected micro-object 116. The micro-object 116 can thus be moved in the chamber 110 by moving the light trap 412 on the photoconductive layer 308. For example, a micro-object 116 can be selected and moved into and/or output of a pen 402 by forming a light trap 412 that traps the micro-object 116 and then moving the light trap 412 on the inner surface 102.

Although illustrated as partial squares in FIG. 4, the pens 402 can alternatively be other shapes. For example, the pens 402 can be partial circles, ovals, rectangles, triangles, or the like. The light trap 412 can similarly have other shapes than the circle shown.

Like pens 302 and 402, the pens 112 can, in some embodiments, also be configured to impede direct flow (e.g., convection flow) of the first medium 122 from a common flow in a flow path 126 into the pens 112 while allowing substantially only diffusive mixing of the first medium 122 from the common flow 314 in a flow path 126 and the second medium inside a pen 112.

The housing 102, however, need not be configured with a single common space for media 114. Rather, the housing 102 can comprise one or more interconnected chambers, channels, or the like for containing media 114 and through which media 114 can flow. FIGS. 5A-7 illustrate examples.

Figure 5A:
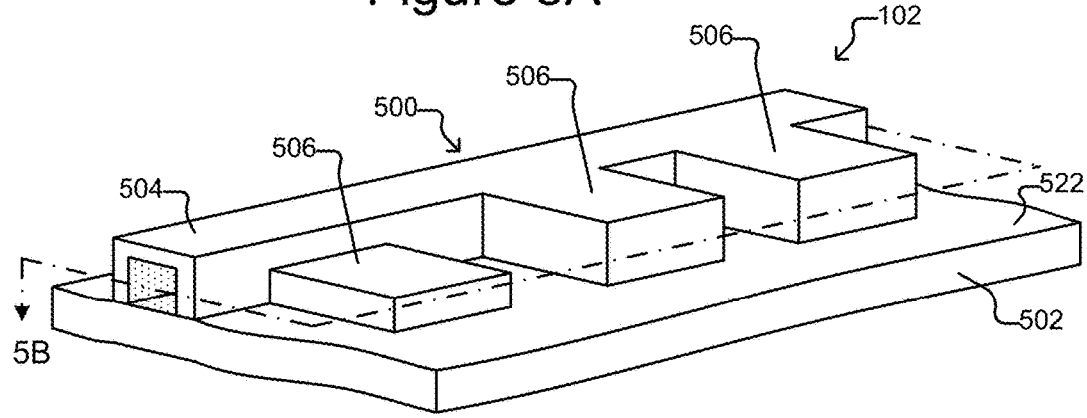
FIG. 5A illustrates an example of a micro-fluidic structure disposed on a base that defines a fluidic channel and pens according to some embodiments of the invention.
Figure 5B:
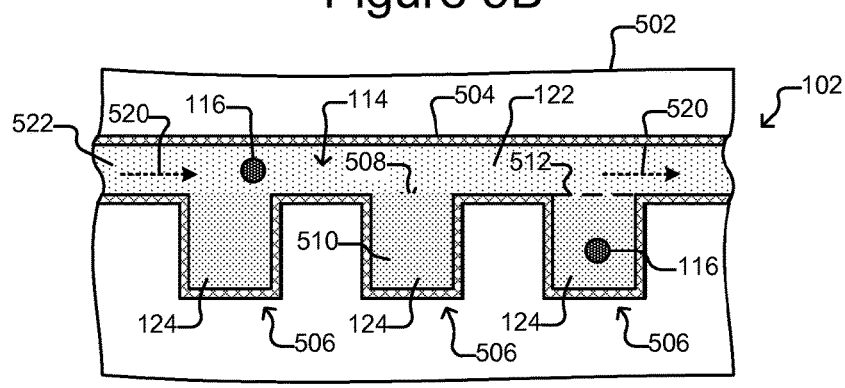
FIG. 5B is a top, cross-sectional view of the micro-fluidic structure and base of FIG. 5A.

As shown in FIGS. 5A and 5B, the housing 102 of the device 100 (see FIGS. 1A-1C) can comprise a base (e.g., a substrate) 502 on which is disposed one or more micro-fluidic structures 500. The base 502 can comprise, for example, the lower wall 206 as discussed above with respect to FIG. 2, and all or part of the top surfaces of the micro-fluidic structure 500 can comprise the upper wall 202 including any variation discussed above.

As shown, the micro-fluidic structure 500 can comprise a channel 504 and pens 506, each of which can comprise an enclosure 510 and an opening 508 to the channel 504. As shown, the pens 506 and the channel 504 can be the same or a different height from the base 502. The channel 504 and pens 506 can correspond to the chamber 110 of FIGS. 1A-1C and 2, and the surface 522 of the base 502 can correspond to the inner surface 120 of the chamber 110 of FIGS. 1A-1C and 2. Thus, in embodiments of the invention in which the housing 102 comprises the base 502 and the OET device of FIG. 2, DEP electrodes can be activated and deactivated in accordance with the light pattern 216 at the surface 522 of the base 502 rather than the inner surface 120 of the chamber 110.

One or more micro-objects 116 can be deterministically selected and moved (e.g., using the detector 220 and selector 118 as discussed above) from the channel 504 (which can be an example of a common space and/or a flow path) through the opening 508 into the enclosure 510 of a pen 506. The micro-object(s) 116 can then be held for a period of time in the pen 506. The opening 508 and enclosure 510 of each pen can be sized and configured and the rate of the flow 520 of media 114 in the channel 504 can be such that the flow 520 creates little to no appreciable convection inside the enclosure 510. Once placed in a pen 506, micro-object(s) 116 thus tend to stay in the pen 506 until actively removed from the pen 506. Diffusion through the opening 508 between media 114 in the channel 504 and the enclosure 510 can provide for inflow into the enclosure 510 from the channel 504 of nutrients for the micro-object(s) 116 in a pen 506 and outflow from the enclosure 510 into the channel 504 of waste from the micro-object(s) 116.

The pens 506 can be structured so that a first medium 122 in the flow 520 in the channel 504 does not flow directly into any of the pens 506, but the structure of the pens 506 allows diffusive mixing of the first medium 122 from the flow 520 through the opening 508 in the pen 506 with a second medium 124 inside the pen 506 generally as discussed above.

The channel 504 and the pens 506 can be physical structures as shown in FIGS. 5A and 5B. For example, the micro-fluidic structure 500 can comprise a flexible material (e.g. rubber, plastic, an elastomer, polydimethylsioxane ("PDMS"), or the like), which can also be gas permeable in some embodiments. Alternatively, the micro-fluidic structure 500 can comprise other materials including rigid materials. Although one channel 504 and three pens 506 are shown, the micro-fluidic structure 500 can comprise more than one channel 504 and more or fewer than three pens 506. As shown in FIG. 5B, a virtual door 512 can optionally be created and removed closing and opening the opening 508 of each of the pens 506. Such virtual doors 512 can be created by activating DEP electrodes at the surface 522 of the base 502 generally as discussed above with regard to the inner surface 120.

Although the channel 504 and pens 506 are illustrated in FIGS. 5A and 5B as physical, the channel 504 and pens 506 can alternatively be virtual. For example, all or part of the channel 504 and/or the pens 506 can be created by activating DEP electrodes at the surface 522 of the base 502 generally as discussed above.

Figure 6A:
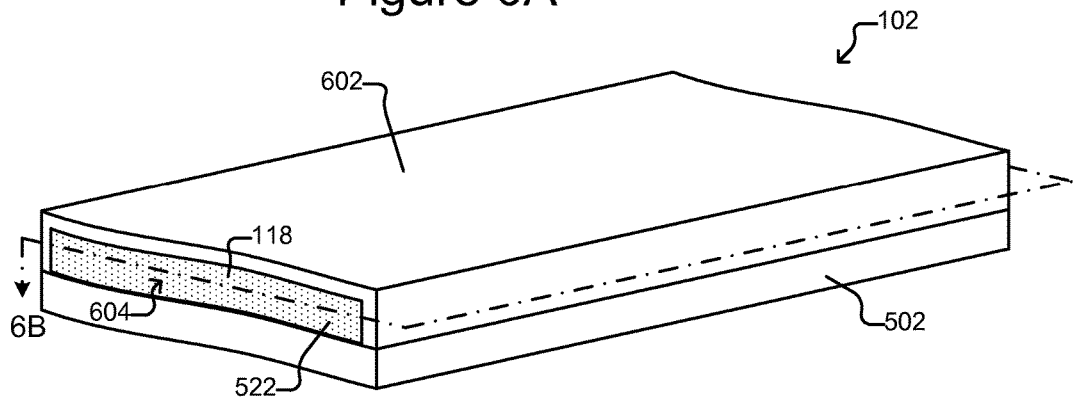
FIG. 6A illustrates an example of a micro-fluidic structure disposed on a base that defines fluid channels and pens according to some embodiments of the invention.
Figure 6B:
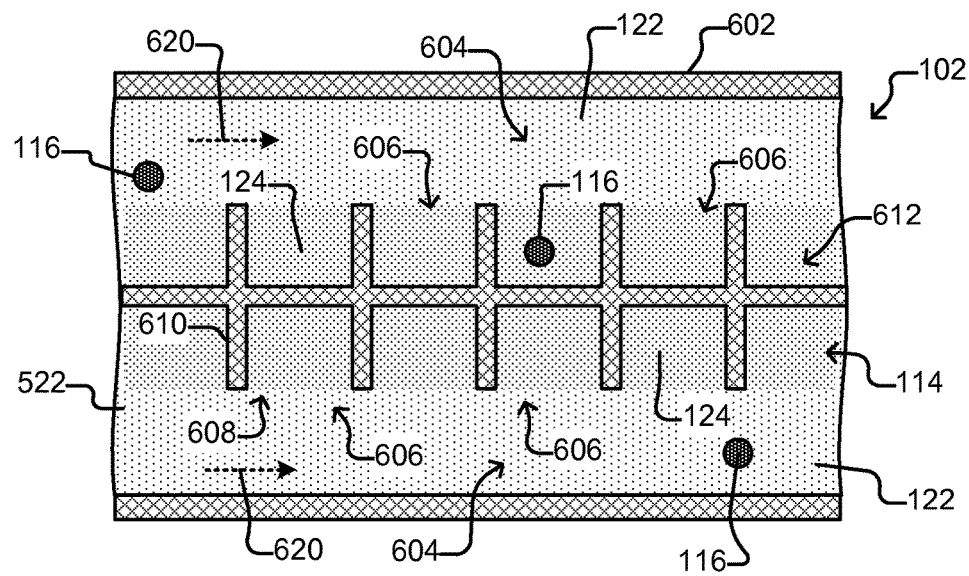
FIG. 6B is a top, cross-sectional view of the micro-fluidic structure and base of FIG. 6A.

In the example shown in FIGS. 6A and 6B, the housing 102 of the device 100 (see FIGS. 1A-1C) can comprise the base 502 of FIGS. 5A and 5B and a micro-fluidic structure 602 disposed on the surface 522 of the base 502. As can be seen in FIG. 6B, the micro-fluidic structure 602 can comprise a pen structure 612, which can comprise pens 606. Each such pen 606 can comprise an enclosure 610 in which a micro-object 116 can be placed and held for a time period. As also shown in FIG. 6B, the micro-fluidic structure 602 can define channels 604, and the opening 608 of each pen 606 can be in fluidic communication (e.g., contact) with media 114 in one of the channels 604.

One or more micro-objects 116 can be deterministically selected (as discussed above) and moved from one of the channels 604 (which can be an example of a common space and/or a flow path) through the opening 608 into the enclosure 610 of a pen 606. The micro-object(s) 116 can then be held in a pen 606 for a period of time. Thereafter, the micro-object(s) 116 can be moved from the enclosure 610 through the opening 608 into the channel 604. Flows 620 of media 114 in the channels 604 can move micro-objects 116 in the channels 604.

Because the openings 608 of the pens 606 are in fluidic communication with a channel 604, the flows 620 of media 114 in the channels 604 can provide nutrients to the micro-objects 116 in the pens 606 and allow for the outflow of waste from the micro-objects 116 during the period of time that the micro-objects 116 are held in the pens 606. The flows 620 in the channels 604 can thus constitute a common flow of media 114 to the pens 606, which like pens 506, can otherwise physically separate and isolate micro-objects 116.

The pens 606 can be structured so that a first medium 122 in a flow 620 in a channel 604 does not flow directly into any of the pens 606, but the structure of the pens 606 allows diffusive mixing of the first medium 122 from a flow 620 through an opening 608 in the pen 606 with a second medium 124 in a pen 606. For example, a pen 606 can be physical (rather than virtual) and the opening 608 of the pen 606 can be oriented in any direction so long as no part of the opening 608 faces directly into a flow 620. A pen 606 can thus impede direct flow of the first medium 122 into the pen 606.

The pens 606 can be physical structures as shown in FIG. 6B. For example, the micro-fluidic structure 600 can comprise any of the materials discussed above with respect to the micro-fluidic structure 500 of FIGS. 5A and 5B. Although two channels 604 and twelve pens 606 are shown in FIG. 6B, the micro-fluidic structure 602 can comprise more or less than two channels 604 and more or fewer than twelve pens 606. Although not shown, a virtual door like door 512 of FIG. 5B can optionally be created at the openings 608 of one or more of the pens 606.

Although the micro-fluidic structure 602 including the pen structure 612 are shown in FIGS. 6A and 6B as physical, all of part of the structure 602 can alternatively be virtual and thus created by activating DEP electrodes at the surface 522 of the base 502 as discussed above with respect to the inner surface 120. For example, all or part of the pen structure 612 can be virtual rather than physical.

Figure 7:
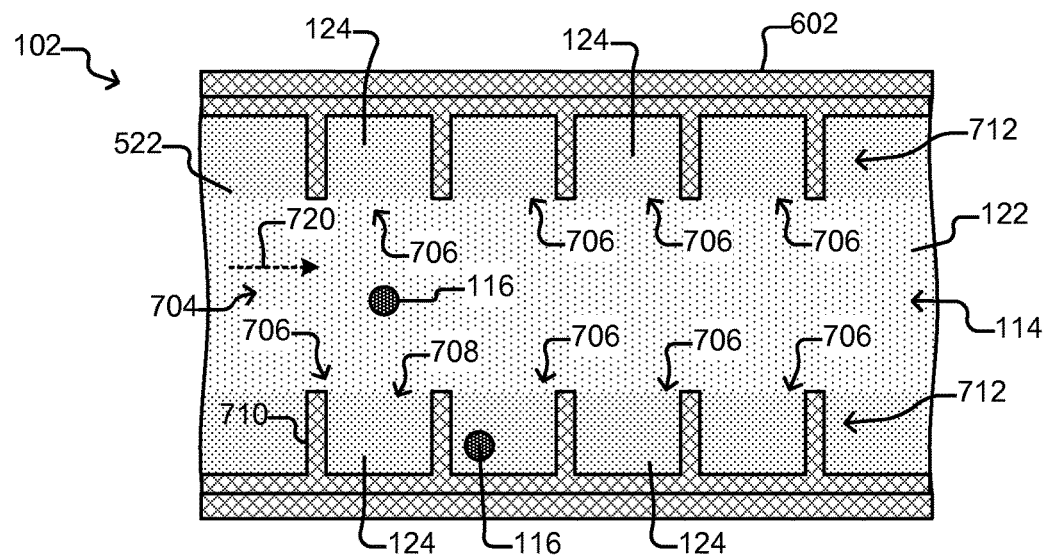
FIG. 7 illustrates an example of a variation of the pens shown in FIG. 6B according to some embodiments of the invention.

FIG. 7 is similar to FIG. 6B except that a channel 704 (which can be an example of a flow path 126) is disposed between pen structures 712 as shown. Otherwise, each pen 706 can be similar to each pen 606. For example, each pen 706 can comprise an enclosure 710 in which a micro-object 116 can be placed and held. As also shown in FIG. 7, the opening 708 of each pen 706 can be in fluidic communication (e.g., contact) with media 114 in the channel 704. One or more micro-objects 116 can be deterministically selected (as discussed above) and moved from the channel 704 (which can be an example of a common space) through the opening 708 into the enclosure 710 of a pen 706, where the micro-object(s) 116 can be held for a period of time. Thereafter, the micro-object(s) 116 can be moved from the enclosure 710 through the opening 708 into the channel 704. The flow 720 of media 114 in the channels 704 can move micro-objects 116 in the channel 704. Alternatively or in addition, the micro-objects 116 can be moved by DEP forces, centrifugal forces, and/or the like.

Because the openings 708 of the pens 706 are in fluidic communication with the channel 704, the flow 720 of media 114 in the channel can also provide nutrients to the micro-objects 116 in the pens 706 and provide for the outflow of waste from the micro-objects 116 during the period of time that the micro-objects 116 are held in the pens 706. The flow 720 in the channel 704 can thus constitute a common flow of media 114 to all of the pens 706.

The pens 706 can be structured so that a first medium 122 in the flow 720 in the channel 704 does not flow directly into any of the pens 706, but the structure of the pens 706 allows diffusive mixing of the first medium 122 in the channel 704 through an opening 708 in the pen 706 with second medium 124 in a pen 706. For example, a pen 706 can be physical and can be oriented so that no opening to the pen 706 faces directly into the flow 720.

Although one channel 704 and twelve pens 706 are shown in FIG. 7, there can be more or fewer. Although not shown, a virtual door like door 512 of FIG. 5B can optionally be created at the openings 708 of one or more of the pens 706. Although the pen structures 712 are shown in FIG. 7 as physical, all or part of the pen structures 702 can alternatively be virtual and thus created by activating DEP electrodes at the surface 522 of the base 502 as discussed above with regard to inner surface 120.

The shape and configuration of the pens 506, 606, 706 (or any pen disclosed herein) illustrated in FIGS. 5A-7 are examples only, and those pens 506, 606, 706 (or any pen disclosed herein) can take other shapes and/or configurations. For example, any of pens 506, 606, 706 (or any pen disclosed herein) can be circular, oval, triangular, or the like rather than square or rectangular. As other examples, any of the pens 506, 606, 706 (or any pen disclosed herein) can be replaced by the pen 806, 826, 906, 926 illustrated in FIGS. 8A-10.

Figure 8A:
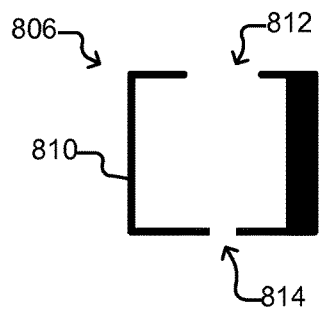
FIGS. 8A, 8B, 9, and 10 illustrate examples of alternative configurations of pens according to some embodiments of the invention.

As shown in FIG. 8A, a pen 806 can comprise an opening 812 (e.g., corresponding to openings 506, 606, 706) that is smaller than the full width of the enclosure 810 (e.g., corresponding to enclosures 510, 610, 710). As also shown in FIG. 8A, a pen 806 can comprise one or more secondary openings 814 (one is shown but there can be more). The opening 812 can be larger than a micro-object 116 (not shown in FIG. 8A), and the secondary opening 814 can be smaller than a micro-object 116. The secondary opening 814 can allow, for example, media 114 (not shown in FIG. 8A) to flow into or out of the pen 806. For example, media 114 can flow into the pen 806 through the opening 812 and out of the pen 806 through the secondary opening 814. As also shown in FIG. 8A, the walls of a pen need not be the same thickness.

Figure 8B:
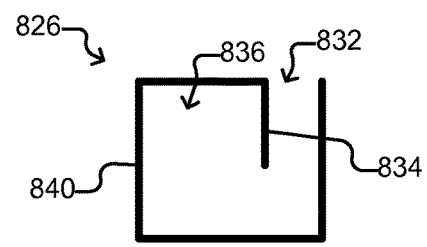

As shown in FIG. 8B, a pen 826 can comprise an inner wall 834 that extends from an opening 832 (e.g., corresponding to openings 508, 608, 708, 812) to create an inner containment space 836 within the enclosure 840 (e.g., corresponding to enclosures 510, 610, 710).

Figure 9:
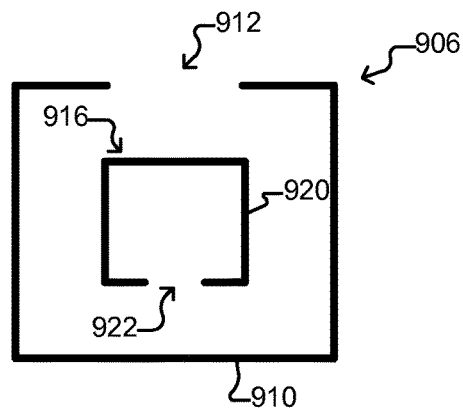

As illustrated in FIG. 9, a pen 906 can comprise one or more additional pens 916 (one is shown but there can be more). For example, one or more inner pens 916 (one is shown but there can be more) comprising an opening 922 and an enclosure 920 can be disposed inside the enclosure 910 of an outer pen 906, which can comprise opening 912. One or more micro-objects 116 (not shown in FIG. 9) can be disposed in the enclosure of each inner pen 916 and the outer pen 906.

Figure 10:
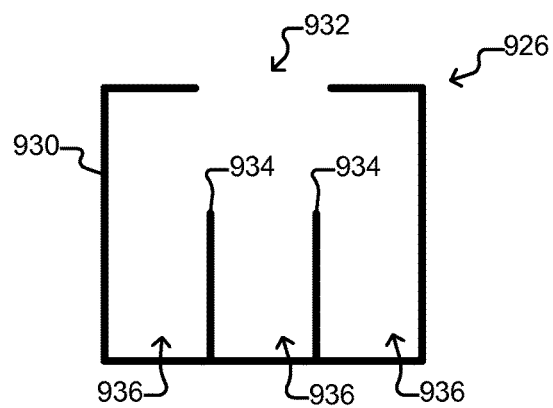

As shown in FIG. 10, a pen 926 (comprising an opening 932 and enclosure 930) can comprise multiple holding spaces 936 (although three are shown, there can be more or fewer) separated by interior walls 934. One or more micro-objects 116 (not shown in FIG. 10) can be disposed in each holding space 936. For example, a different type of micro-object 116 can be disposed in each holding space 936.

Any of the pens disclosed herein can be configured to be like or to have any of the characteristics of the pens 806, 826, 906, 926 illustrated in FIGS. 8A-10.

Regardless of the configuration of the pens, micro-objects 116 can be deterministically selected and moved from the flows 520, 620, 720 in the channels 504, 604, 704 into pens 506, 606, 706 in FIGS. 5A-7 (including the variations of the pens 506, 606, 706 illustrated in FIGS. 8A-10) by any of a variety of mechanisms. FIGS. 11A-12B illustrate examples in which the OET device of FIG. 2 is used to do so. In FIGS. 11A-12B, the channel 1104 can be any of the channels 504, 604, 704; the pen 1106 can be any of the pens 506, 606, 706; and the flow 1120 of media 114 can be any of the flows 520, 620, 720 in FIGS. 5A-7.

Figure 11A:
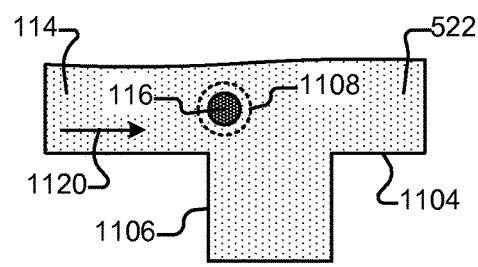
FIGS. 11A and 11B illustrated selecting and moving a micro-object using a light trap according to some embodiments of the invention.
Figure 11B:
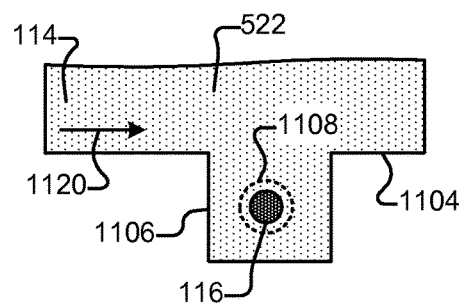

As shown in FIG. 11A, a micro-object 116 can be deterministically selected in the flow 1120 in the channel 1104 by creating a light trap 1108 (e.g., like light trap 304) that traps the micro-object 116, which can trap the micro-object 116 in the trap 1108. As shown in FIG. 11B, the light trap 1108 can then be moved from the channel 1104 into the pen 1106, where the micro-object 116 can be released from the light trap 1108. The light trap 1108 can be like and can be created and moved on the surface 522 of the base 502 by the OET device of FIG. 2 in the same way as light traps 304, 412 are created and moved on the inner surface 120 as discussed above.

Figure 12A:
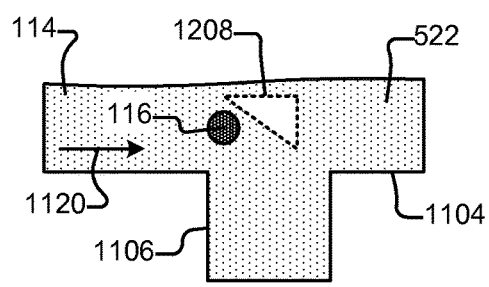
FIGS. 12A and 12B show selecting and moving a micro-object using a virtual barrier according to some embodiments of the invention.
Figure 12B:
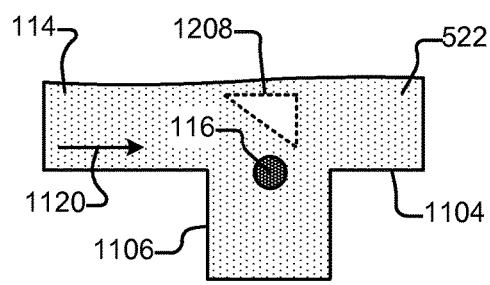

As shown in FIG. 12A, a micro-object 116 can be deterministically selected in the flow 1120 in the channel 1104 by creating a virtual barrier 1208 in the path of the micro-object 116 in the channel 1104. As illustrated in FIG. 12B, the virtual barrier 1208 can deflect the micro-object 116 into the pen 1106. The virtual barrier 1208 can be created by activating DEP electrodes on the surface 522 of the base 502 using the OET device of FIG. 2 generally as discussed above. Once the selected micro-object 116 is deflected into the pen 1106, the virtual barrier 1208 can be removed from the channel 1104.

As mentioned above, micro-objects 116 can be contained in any of the pens disclosed herein for a period of time after which the micro-objects 116 can be removed from the pens. In some embodiments, micro-objects 116 can be removed from pens in any of the ways illustrated in FIGS. 11A-12B.

For example, a light trap 1108 can be formed that traps a micro-object 116 in a pen 1106 and the light trap 1108 can be moved out of the pen 1106 into the channel 1104, which is the reverse of the process shown in FIGS. 11A and 11B. Once in the channel 1104, the light trap 1108 can be turned off, releasing the micro-object 116 into the flow 1120 of media 114 in the channel 1104.

As another example, a virtual barrier similar to the barrier 1208 shown in FIGS. 12A and 12B can be formed in a pen 1106 to nudge a micro-object 116 out of the pen 1106 into the flow 1120 of media 114 in the channel 1104. The foregoing is the reverse of the process shown in FIGS. 12A and 12B.

As yet another example, any of the physical pens disclosed herein can be configured like the outputting mechanisms 800 disclosed in the aforementioned U.S. patent application Ser. No. 13/856,781. In such a configuration, the pens can be configured like the expressing mechanism 804 in the foregoing patent application, and a striking mechanism (not shown) like the striking mechanism 802 in the foregoing patent can be provided to express the micro-objects 116 from the pens.

Figure 13A:
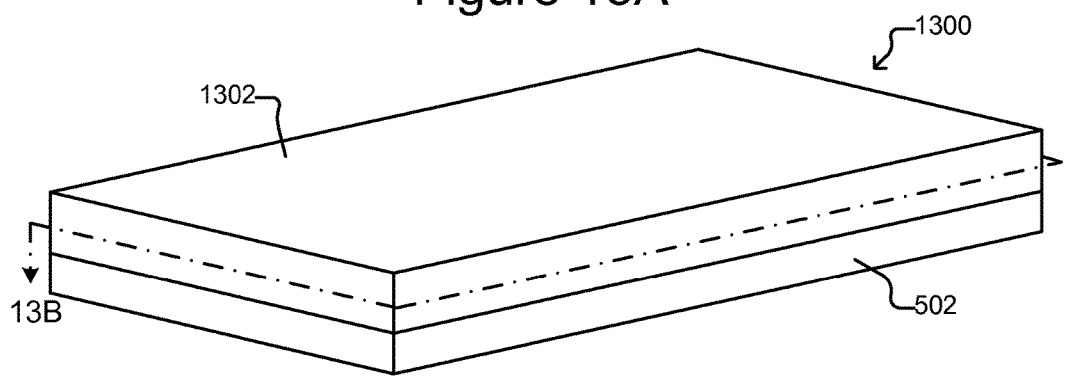
FIG. 13A illustrates an example of a micro-fluidic structure disposed on a base that defines a fluid chamber and pens according to some embodiments of the invention.
Figure 13B:
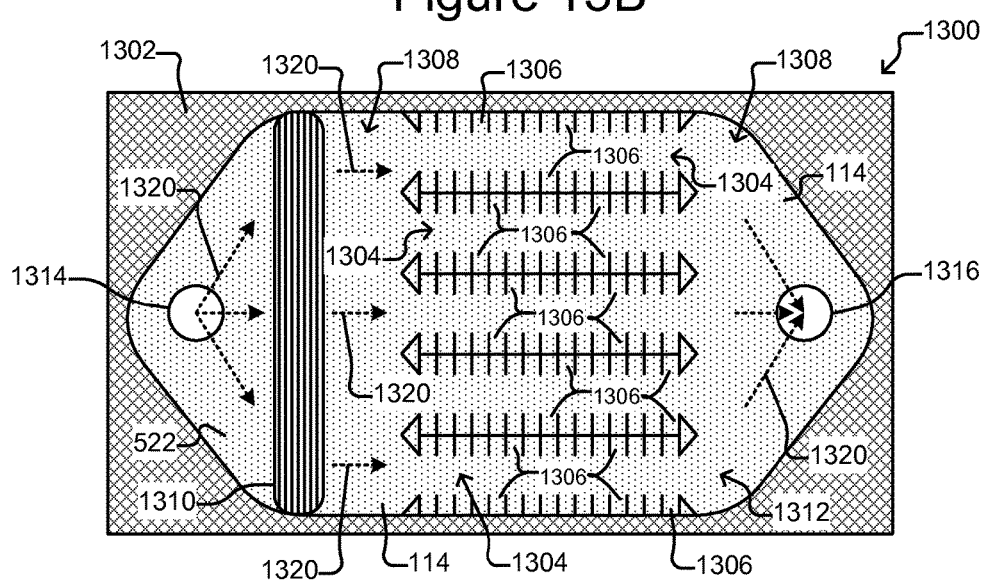
FIG. 13B is a top, cross-sectional view of the micro-fluidic structure and base of FIG. 13A.

FIGS. 13A and 13B illustrate a micro-fluidic device 1300 that can be an example of the device 100 of FIGS. 1A-1C in which the base 502 and a micro-fluidic structure 1302 are examples of the housing 102, the chamber 1308 is an example of the chamber 110, the inlet 1314 is an example of the inlet 104, the outlet 1316 is an example of the outlet 106, and the pens 1306 are examples of the pens 112. (Compare to FIGS. 1A-1C.)

As shown in FIGS. 13A and 13B, the device 1300 can comprise a micro-fluidic structure 1302 disposed on the base 502 (which is described above with respect to FIGS. 5A and 5B). As can be seen in FIG. 13B, the micro-fluidic structure 1302 and base 502 can define a chamber 1308 for media 114 and micro-objects 116. Media 114 with micro-objects 116 can be input into the chamber 1308 through an inlet 1314 and output from the chamber 1308 through an outlet 1316. A flow 1320 of media 114 can thus be provided in the chamber 1308 from the inlet 1314 to the outlet 1316. The inlet 1314 and outlet 1316 can be the same as or similar to the inlet 104 and outlet 106 of FIGS. 1A-1C as discussed above. The channels 1304 are examples of common spaces and/or flow paths for media 114.

As also shown in FIG. 13B, a gas exchanger 1310 and an array 1312 of pens 1306 and channels 1304 can be disposed in the chamber 1308 between the inlet 1314 and the outlet 1316 and thus in the flow 1320 of media 114. The flow 1320 of media 114 can thus pass from the inlet 1314 through the gas exchanger 1310, through the channels 1304 of the pen array 1312, and out the outlet 1316. Alternatively, the inlet 1314 can be located between the gas exchanger 1310 and the pens 1304, and the gas exchanger 1310 can thus be located upstream from the inlet 1314.

The channels 1304 and pens 1306 can be like any of the channels and pens discussed herein. For example, the channels 1304 can be like any of channels 504, 604, 704, 1104, 1204 including any variation of those channels discussed above, and the pens 1306 can be like any of pens 112, 302, 402, 506, 606, 706, 806, 906, 1106, 1206 including any variation of those pens discussed above.

Openings of the pens 1306 can be in fluidic communication (e.g., contact) with one of the channels 1304. As micro-objects 116 (not shown in FIGS. 13A and 13B) move with the flow 1320 of media 114, ones of the micro-objects 116 can be selected in a channel 1304 and moved into a pen 1306. A micro-object 116 can be deterministically selected in a channel 1304 and moved into a pen 1306 using any technique or mechanism discussed above (e.g., with light traps like light traps 304, 412, 1108; with a virtual barrier like barrier 1208; or the like). The flow 1320 of media 114 can also be a common flow that carries nutrients to and provides for the outflow of waste from micro-objects 116 in the pens 1306, which can otherwise isolate micro-objects 116 from each other. Moreover, each of the pens 1306 can be structured so that media 114 (e.g., the first medium 122 shown in FIGS. 1B and 1C) in a flow 1320 in a channel 1304 does not flow directly into any of the pens 1306, but the structure of each pen 130 can allow diffusive mixing of media 114 from a flow 1320 in a channel 1304 and media 114 (e.g., the second medium 124 shown in FIGS. 1B and 1C) in a pen 1306 generally as discussed above.

Figure 14:
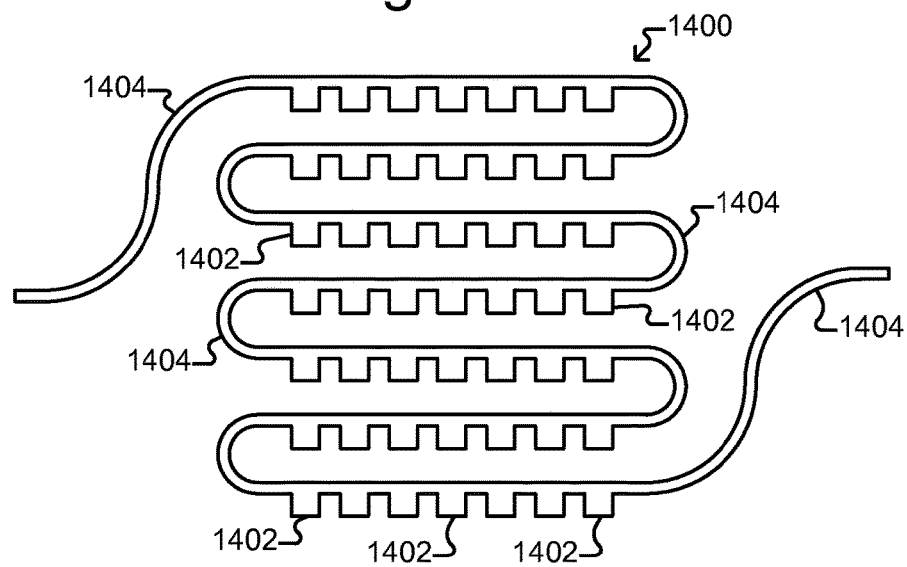
FIGS. 14 and 15 show examples of alternative configurations of the pen array of FIG. 13B according to some embodiments of the invention.
Figure 15:
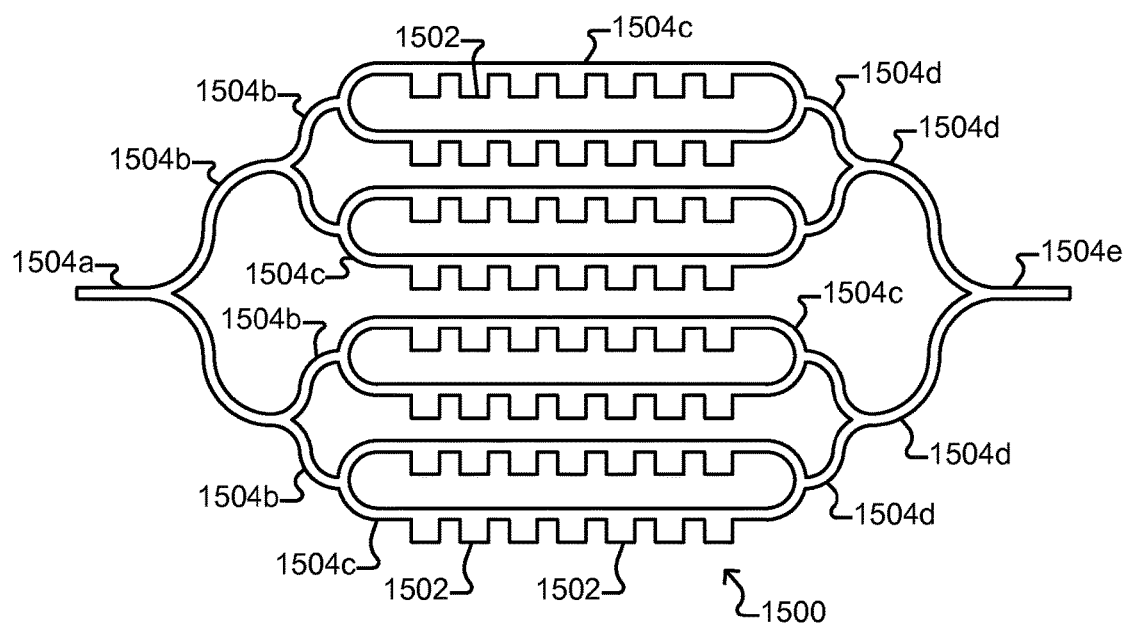

The configuration of the pen array 1312 in FIG. 13B is but an example. FIGS. 14 and 15 illustrate examples of alternative configurations.

As shown in FIG. 14, a pen array 1400 can comprise rows of pens 1402, and openings of the pens 1402 can be in fluidic communication (e.g., contact) with a single channel 1404. The pen array 1400 and channel 1404 can replace the pen array 1312 and channels 1304 in FIG. 13B, and the flow 1320 of media 114 in FIG. 13B can be through the channel 1404.

The pen array 1500 and channels 1504 in FIG. 15 can also replace the pen array 1312 and channels 1304 in FIG. 13B. As shown in FIG. 15, the pen array 1500 can comprise rows of pens 1502 with openings in direct fluidic communication with channels 1504c. A plurality of first branching channels 1504b can connect an input channel 1504a to the channels 1504c that flow directly past the pens 1502. Other (second)

branching channels 1504*d* can connect the channels 1504*c* to an output channel 1504*e*. The flow 1320 of media 114 in FIG. 13B can be into the first channel 1504*a*, through branching channels 1504*b* to the channels 1504*c* in direct fluidic communication with the pens 1502, through other branching channels 1504*d* to the second channel 1504*e*.

The channels 1404, 1504 in FIGS. 14 and 15 can be like channels 1304 as discussed above. The pens 1402, 1502 can likewise be like pens 1306 as discussed above. The channels 1404, 1504 can be examples of common spaces and/or flow paths. Each pen 1402, 1502 can be structured so that media 114 (e.g., the first medium 122 in FIGS. 1B and 1C) in a flow in a channel 1404, 1504 does not flow directly into the pen 1402, 1502, but the structure of each pen 1402, 1502 can allow diffusive mixing of media from a flow in a channel 1404, 1504 and media (e.g., the second medium 124 in FIGS. 1B and 1C) in a pen 1402, 1502 generally as discussed above.

Figure 16:
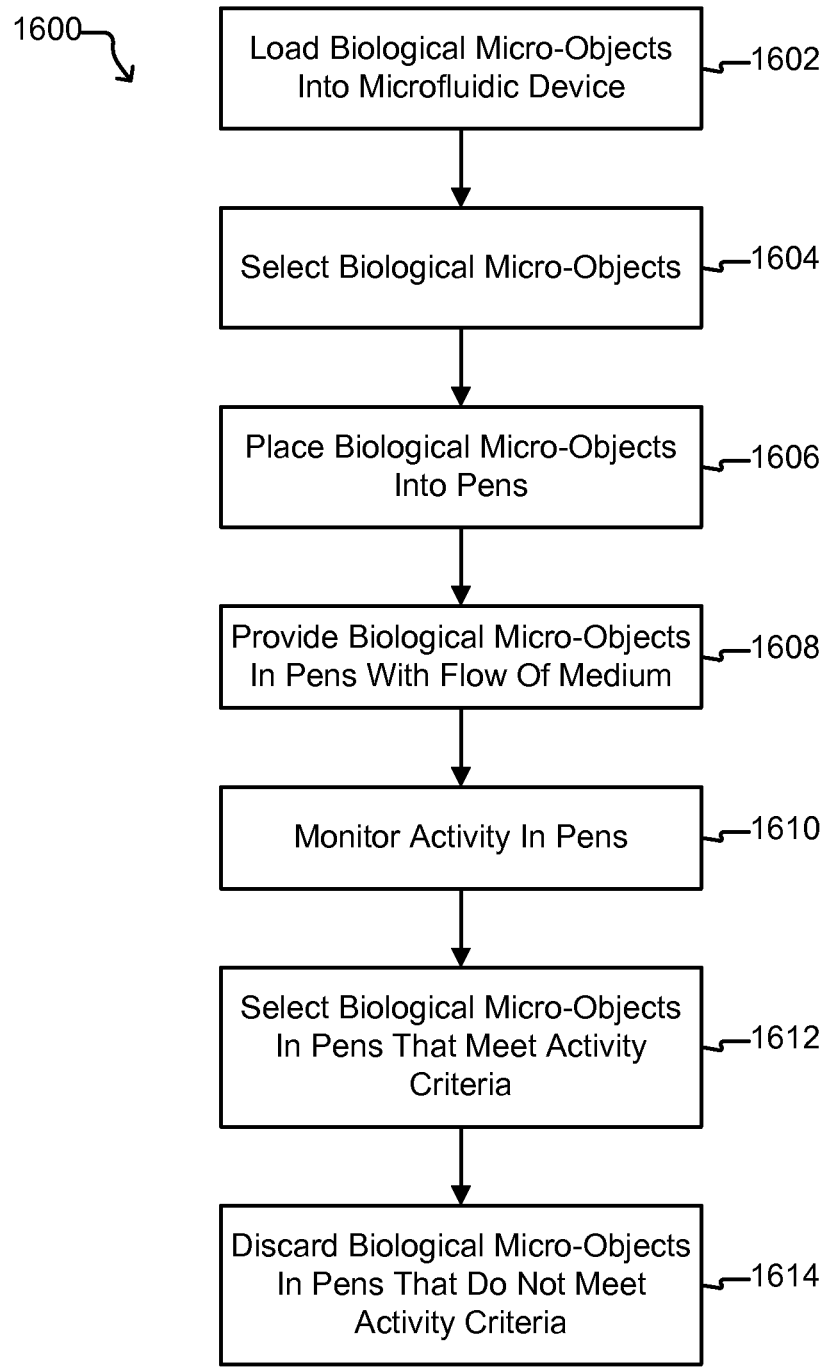
FIG. 16 shows an example of a process that includes placing biological micro-objects into pens in a micro-fluidic device according to some embodiments of the invention.

FIG. 16 illustrates an example of a process 1600 for processing biological micro-objects in pens. The process 1600 can be performed using any of the micro-fluidic devices discussed above or similar devices. For example, the process 1600 can be performed using the micro-fluidic devices 100 and 1300 including any variation of those devices discussed above (e.g., as illustrated in FIGS. 2-12B, 14, and 15).

As shown in FIG. 16, at step 1602, the process 1600 can load biological micro-objects into a micro-fluidic device. For example, the process 1600 can introduce into the chamber 110 of the device 100 of FIGS. 1A-1C through the inlet 104 micro-objects 116 in media 114. As another example, the process 1600 can introduce into the chamber 1308 of the device 1300 of FIGS. 13A and 13B micro-objects 116 in media 114 through the inlet 1314.

At step 1604, the process can select individual ones of the biological micro-objects loaded at step 1602. For example, the process 1600 can select a sub-set of less than all of the micro-objects 116 in media 114 that have a particular characteristic. The micro-objects 116 can be monitored, for example, using the imaging device 220 of FIG. 2. At step 1604, one micro-object 116 having a particular desired characteristic can be deterministically selected and loaded into one pen such that step 1604 results in one and only one micro-object 116 in each of a plurality of the pens. Alternatively, more than one micro-object 116 can be loaded into a pen.

At step 1606, the process 1600 can place the micro-objects 116 selected at step 1604 into pens of the micro-fluidic device. For example, at step 1606, the process 1600 can place selected micro-objects 116 into the pens 112, 302, 402, 506, 606, 706, 806, 906, 1106, 1206, 1306, 1402, 1502 using any of the techniques discussed above. As noted above and illustrated throughout the drawings, the foregoing pens can physically separate micro-objects 116 one from another. That is, each pen can physically separate the micro-object 116 or micro-objects 116 in the pen from all other micro-objects 116 in the micro-fluidic device 100, 1300. After placing selected micro-objects 116 in the pens at step 1606, the process 1600 can keep the micro-objects 116 in the pens for a time period.

At step 1608, the process 1600 can provide a flow of liquid media 114 to the pens. Step 1608 can be accomplished by providing any of the flows 314, 314, 520, 620, 720, 1120, 1320 in the chambers 110, 1308 or channels 504, 604, 704, 1104 as discussed. It is noted that, at step 1606, individual micro-objects 116 can be physically isolated from each other by being placed in physically separated pens, but at step 1608, those micro-objects 116 in the pens can be provided with the same flow of media 114. As noted above, the pens 112, 302, 402, 506, 606, 706, 806, 906, 1106, 1206, 1306, 1402, 1502 can be structured to impede direct flow of media 114 (e.g., the first medium 122 shown in FIGS. 1B and 1C) from the flows 314, 314, 520, 620, 720, 1120, 1320 in the chambers 110, 1308 or channels 504, 604, 704, 1104 into the pens 112, 302, 402, 506, 606, 706, 806, 906, 1106, 1206, 1306, 1402, 1502 while allowing diffusive mixing of media 114 (e.g., the first medium 122 shown in FIGS. 1B and 1C) from the flows 314, 314, 520, 620, 720, 1120, 1320 and media 114 (e.g., the second medium 124 shown in FIGS. 1B and 1C) inside the pens.

As mentioned, the micro-objects 116 placed into the pens at step 1606 can be kept in the pens for a time period during which step 1608 can provide the micro-objects 116 with the flow of media 114, which through the diffusive mixing discussed above can provide the micro-objects 116 in the pens with nutrients and provide for the outflow of waste from the micro-objects 116. At step 1610, the process 1600 can monitor one or more biological activities of the micro-objects 116 in the pens. Examples of such biological activities can include clone production, secretion of certain biological substances, or the like. The monitoring at step 1610 can be continuous during the time period, periodically during the time period, at the end of the time period, or the like. The monitoring at step 1610 can be performed in any manner suitable for analyzing biological activities of the micro-objects 116. For example, the monitoring at step 1610 can be performed using the imaging system 220 of FIG. 2, with sensors (not shown) in or adjacent the pens, or the like.

At step 1612, the process 1600 can select the micro-objects 116 in the pens that meet a predetermined criteria, threshold, or condition associated with the biological activity or state monitored at step 1610. The micro-objects 116 selected at step 1612 can be removed from the pens for further processing or use. For example, the selected micro-objects 116 can be removed from the pens using any technique or process discussed above. As another example, one or more micro-objects 116 can be removed from a pen by piercing the housing with a needle-like aspirator (not shown), and removing the micro-objects 116 with the aspirator. A specific, controlled number of micro-objects 116 can be removed, for example, by selecting and removing that number of micro-objects 116 or, if the micro-objects 116 are biological cells, removing all of the cells when a colony of cloned cells reaches the desired number.

At step 1614, the process 1600 can discard the micro-objects 116 not selected at step 1612, which are the micro-objects 116 that do not meet the predetermined criteria, threshold, or condition associated with the biological activity or state monitored at step 1610.

Figure 17:
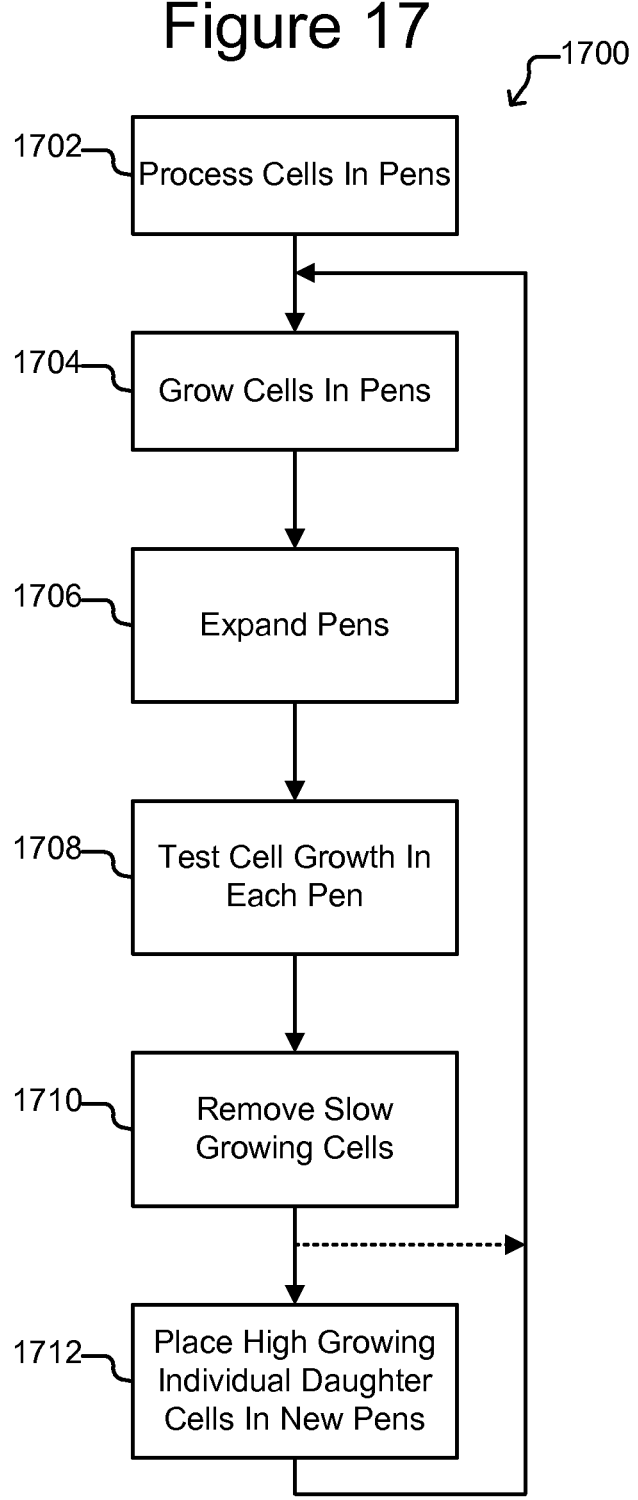
FIG. 17 illustrates a process showing an example of operation of the device of FIG. 1A configured with the OET device of FIG. 2 according to some embodiments of the invention.

FIG. 17 illustrates an example process 1700 for growing colonies of cloned cells from a single parent cell according to some embodiments of the invention. The process 1700 can be an example of the process 1600 of FIG. 16. For example, the process 1700 can start after steps 1602 and 1604 of FIG. 16 are performed; steps 1702-1706 can be performed during steps 1606 and 1608; step 1708 can be an example of step 1610; step 1710 can be an example of step 1614; and step 1712 can be an example of step 1612.

For ease of illustration and discussion the process 1700 is discussed below as performed with the device 100 configured with the OET device of FIG. 2 for creating and manipulating the virtual pens 302 of FIG. 3. The process 1700, however, can be performed with other configurations of the device 100 or the device 1300 in which the pens are virtual pens.

Figure 18A:
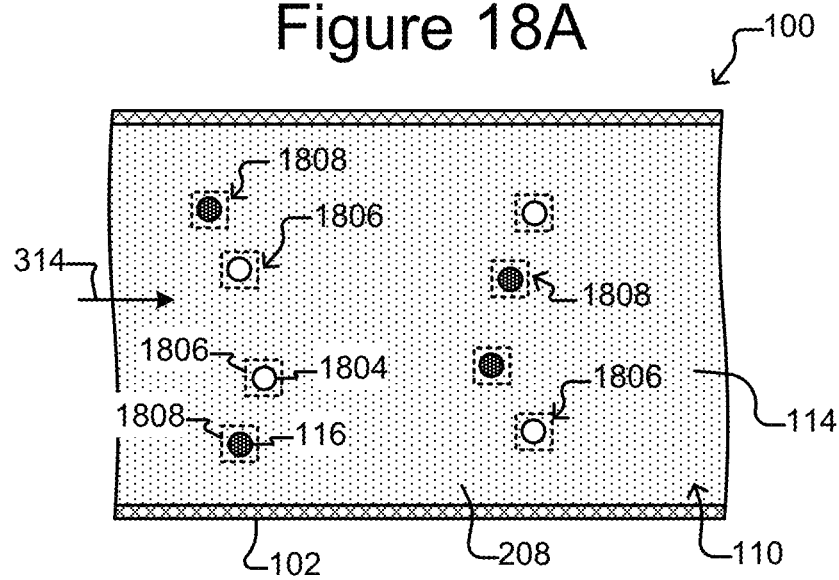
FIGS. 18A-18C illustrate an example of processing cells in accordance with a step of FIG. 17.
Figure 18B:
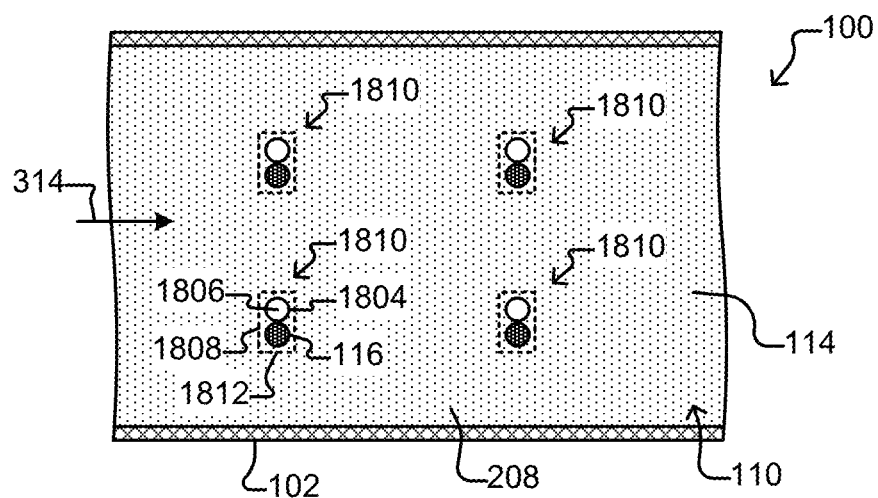
Figure 18C:
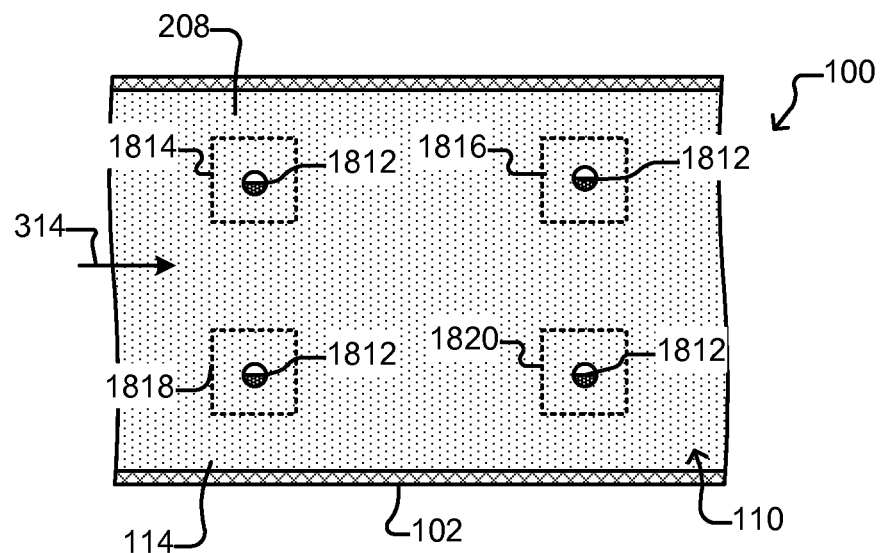

As shown in FIG. 17, at step 1702, the process 1700 can process cells in pens. Such processing can include fusing two cells into one cell, transfecting a cell by injecting a biological vector into a cell, or the like. FIGS. 18A-18C illustrate an example.

As shown in FIG. 18A, two different types of micro-objects 116 and 1804 can be placed in media 114 in the chamber 110. The OET device of FIG. 2 can generate light traps 1806, 1808 (e.g., like light trap 304) to select one of the first cell type 116 and one of the second cell type 1804. The light traps 1806 and 1808 can then be moved into contact such that the first cell type 116 and the second cell type are in contact as shown in FIG. 18B. Such paired cells 1810 can then be subjected to one or more treatments (e.g., including in the flow 314 a fusing chemical (e.g., polyethylene glycol (PEG), the Sendai virus, piercing the membranes of one of the cells 116, 1804, electric fields, pressure, or the like)) that fuse the paired cells 1810 together to form a fused cell 1812 as shown in FIG. 18C. That is, each fused cell 1812 can comprise one of the first cell types 116 and one of the second cell types 1804 fused together. The light traps 1806 and 1808 can be like and can be created and manipulated like the light trap 304, 412 as discussed above including any variation thereof.

As also shown in FIG. 18C, individual fused cells 1812 can be placed in virtual pens 1814, 1816, 1818, 1820. Although four pens 1814, 1816, 1818, 1820 are shown, there can be more or fewer. The virtual pens 1814, 1816, 1818, 1820 can be the same as or similar to the pens 302 of FIG. 3 as described above.

Alternatively, element 1804 in FIG. 18A can be a biological vector to be transfected into a micro-object 116. In such a case, each cell 1812 in FIG. 18C can be one of the micro-objects 116 transfected with a vector 1804.

As yet another alternative, the cells 1812 in FIG. 18C (whether fused cells or transfected cells) can be processed in another device and then placed into the pens 1814, 1816, 1818, 1820. In such an alternative, step 1702 is not included in the process of FIG. 17. As a still further alternative, cells 1812 can be simple cells rather than fused or transfected cells.

Figure 19:
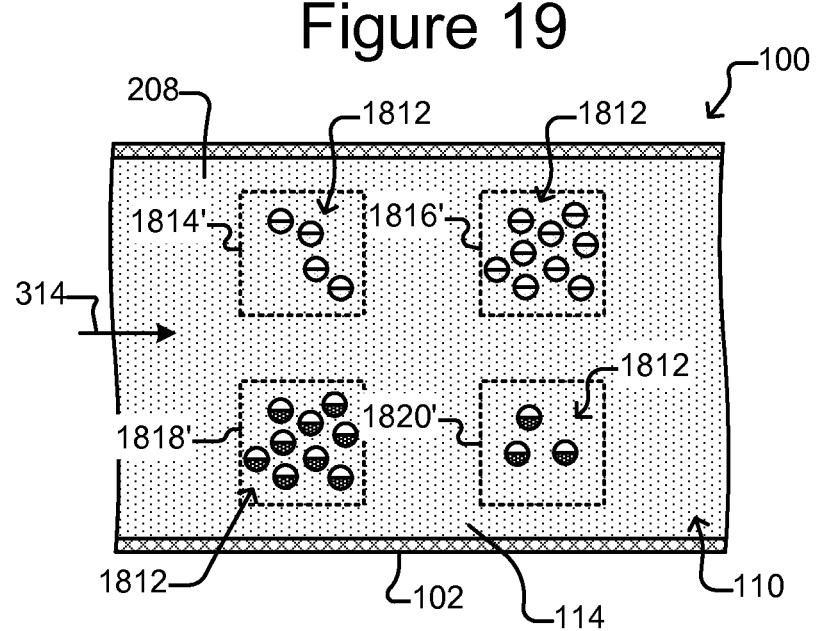
FIG. 19 illustrates an example of expanding pens as clones grown in the pens according to a step of FIG. 17.

Referring again to FIG. 17, at step 1704, clones can be grown in each pen 1814, 1816, 1818, 1820 from the cell 1812 in the pen. This can be facilitated by including a growth medium in the flow 314 through the chamber 114. At step 1706, the pens 1814, 1816, 1818, 1820 can be expanded as the clones grow in each pen. FIG. 19 illustrates an example. As shown in FIG. 19, as the number of cells 1812 in each pen 1814, 1816, 1818, 1820 increases, the size of the pens 1814', 1816', 1818', 1820' can be expanded to accommodate the growing clone populations in each pen.

At step 1708 of FIG. 17, each pen 1814, 1816, 1818, 1820 can be examined and clone growth in the pen can be analyzed. For example, a fluorescent label (e.g., a biological fluorescent compound that fluoresces when stimulated or otherwise) that binds to the clones can be included in the flow 314 through the chamber 110. The level that each pen 1814, 1816, 1810, 1820 fluoresces can then be analyzed to determine clone growth in each pen.

Figure 20:
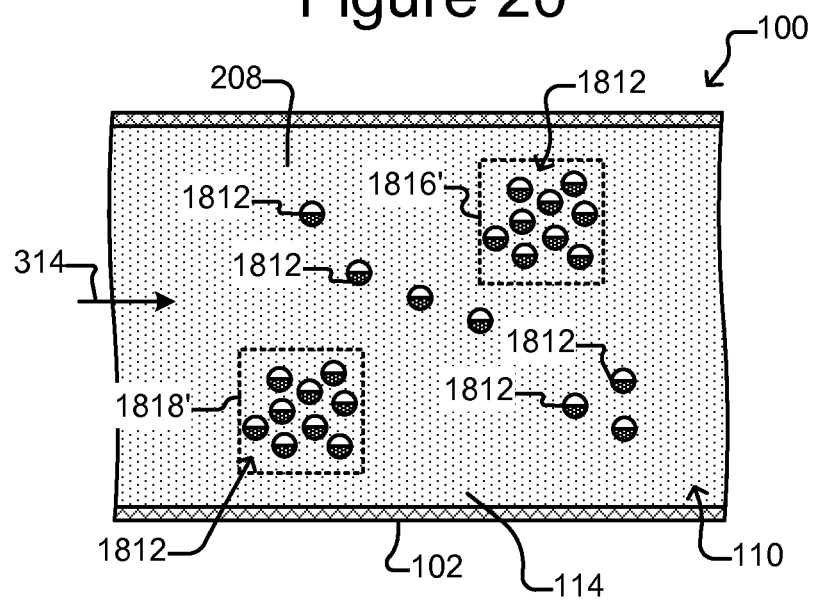
FIG. 20 illustrates an example of turning off pens in which clones are growing too slowly and flushing the clones in those pens away according to a step of FIG. 6.

At step 1710, the clones in the pens 1814, 1816, 1818, 1820 in which the clones 1812 are growing at less than a minimum amount (or are otherwise undesirable) can be discarded. FIG. 20 illustrates an example. For purposes of the example illustrated in FIG. 20, it is assumed that at step 1710 it was determined that the clones 1812 in pens 1814', 1820' of FIG. 19 grew less than a minimum threshold amount and are to be discarded. As shown in FIG. 20, the pens 1814', 1820' can be turned off, freeing the clones 1812 in those pens. The pens 1814', 1820' can be turned off simply by removing from the light pattern 216 being directed into the housing 102 FIG. 2 the light that corresponds to pens 1814', 1820'. The now freed clones 1812 that were in pens 1814', 1820' can be flushed out of the chamber 110 (e.g., by flow 314) and discarded.

Figure 21:
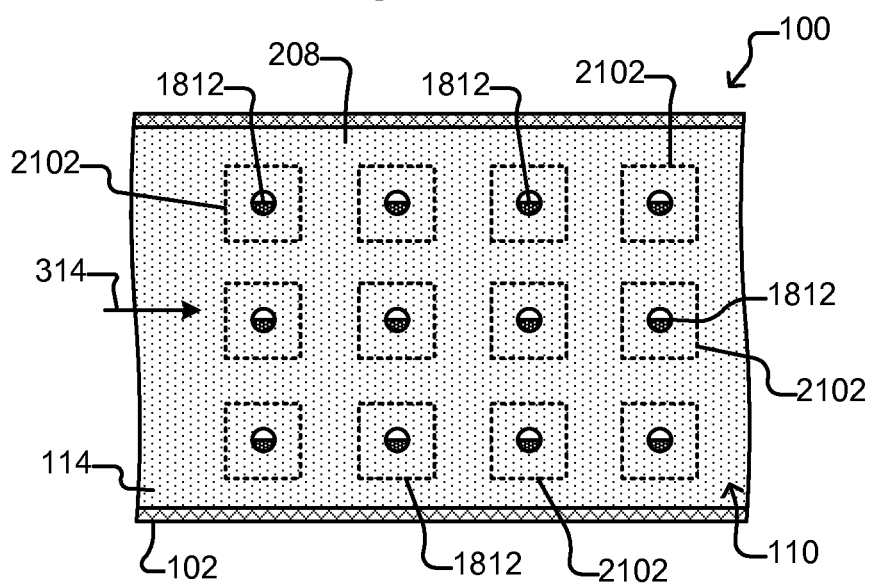
FIG. 21 illustrates an example of placing daughter clones in new pens according to a step of FIG. 17.

As shown in FIG. 17, the steps 1704 through 1710 can be repeated to continue growing clones 1812 in the pens 1816', 1818'. Alternatively, at step 1712, individual ones of the clones 1812 from pens 1814', 1820' can be selected and placed as daughter clones in new pens, and the steps 1704 through 1710 can be repeated to grow, test, and discard slow growers in the new pens. FIG. 21 shows an example in which individual daughter clones 1812 from the pens 1816', 1818' in FIG. 20 are selected and each placed in a new pen 2102. The new pens 2102 can be created and manipulated in the same way that pens 1814, 1816, 1818, 1820 are created and manipulated as discussed above. Individual daughter clones 1812 can be selected and moved generally as discussed above (e.g., with light traps like light trap 304, 412 of FIG. 4).

FIG. 22 illustrates a process 2200 that is a variation of the process 1700 of FIG. 17.

As shown in FIG. 22, one or more cells can be held in and secrete into the pens. For example, as shown in FIG. 18C, a cell 1812 can be disposed in each of the pens 1814, 1816, 1818, 1820. Alternatively, there can be more than one cell 1812 in each pen 1814, 1816, 1818, 1820. The cells 1812 can be fused or transfected cells as discussed above with respect to FIGS. 18A-18C. Alternatively, cells 1812 can be simple cells rather than fused or transfected cells.

At step 2204 of FIG. 22, each pen 1814, 1816, 1818, 1820 can be examined and the productivity of the cells 1812 in the pen can be analyzed. For example, one or more cells 1812 can be removed from each pen 1814, 1816, 1818, 1820 and observed, tested, or the like to determine the secretion productivity of the removed cells 1812.

At step 2206, the pens 1814, 1816, 1818, 1820 in which the cells 1812 are secreting at less than a threshold level can be discarded. This can be accomplished generally as shown in FIG. 20 and discussed above. That is, pens 1814, 1816, 1818, 1820 that contain low producing cells 1812 can be turned off and the low performing cells 1812 washed away generally in accordance with the discussion of FIG. 20 above.

Referring again to FIG. 22, the steps 2202 through 2206 can be repeated to continue to have the cells 1812 in the remaining pens secrete, to test the secretion productivity of the cells in each pen, and discard cells 1812 in low producing pens. Alternatively, at step 2208, individual ones of the high producing cells 1812 can be selected and placed as daughter cells in new pens (e.g., generally in accordance with the example shown in FIG. 21), and the steps 2202 through 2206 can be repeated to have the daughter cells secrete in their new pens, test the secretion productivity of the daughter cells in each pen, and discard daughter cells in low secreting pens.

Although specific embodiments and applications of the invention have been described in this specification, these embodiments and applications are exemplary only, and many variations are possible.

We claim:
1. A micro-fluidic device comprising:
a housing comprising a substrate and a micro-fluidic structure disposed on a surface of said substrate, wherein said substrate and said micro-fluidic structure define an interior chamber for holding a first liquid medium and biological micro-objects suspended therein, and wherein said micro-fluidic structure comprises (i) a channel providing a flow path for the first liquid medium, and (ii) a plurality of physical holding pens,
wherein each holding pen of said plurality comprises
an enclosure, and
a single opening to said channel,
said enclosure enclosing an interior space structured to hold a biological micro-object suspended in a second liquid medium, and
said opening oriented such that no part is facing directly into said flow path of said channel, whereby, when said channel contains a flow of said first liquid medium and said holding pen contains said second liquid medium, a direct flow of said first liquid medium into said second liquid medium in said interior space is impeded while diffusive mixing of said first liquid medium with said second liquid medium in said interior space is allowed; and
wherein said surface of said substrate comprises dielectrophoresis (DEP) electrodes configured to be selectively activated and deactivated.

2. The micro-fluidic device of claim 1, wherein at least one holding pen of said plurality comprises an inner wall extending from said opening into said enclosure.

3. The micro-fluidic device of claim 2, wherein said inner wall of said at least one holding pen comprises a barrier between said opening of said holding pen and an inner containment space within said enclosure of said holding pen.

4. The micro-fluidic device of claim 1, wherein at least one of said holding pens further comprises an inner pen comprising an enclosure and an opening, wherein said inner pen is disposed inside said enclosure of said at least one holding pen.

5. The micro-fluidic device of claim 1, wherein:
at least one holding pen of said plurality comprises holding spaces separated by interior walls disposed inside said enclosure of said at least one holding; and
each said holding space is configured to hold one of said biological micro-objects.

6. The micro-fluidic device of claim 1 further comprising means for selectively creating and removing dielectrophoresis (DEP) doors at any of said openings of said plurality of holding pens.

7. The micro-fluidic device of claim 1 further comprising:
an inlet into said housing to said chamber; and
an outlet from said housing from said chamber.

8. The micro-fluidic device of claim 7, wherein said channel and said plurality of holding pens are disposed in said chamber between said inlet and said outlet.

9. The micro-fluidic device of claim 8 further comprising a gas exchanger disposed in said chamber between said inlet and said plurality of holding pens.

10. The micro-fluidic device of claim 1 further comprising a gas exchanger disposed in said housing.

11. The micro-fluidic device of claim 1 further comprising sensors for monitoring a biological activity of said micro-objects in said holding pens.

12. The micro-fluidic device of claim 1, wherein
(i) said DEP electrodes comprise hardwired electrical connections
(ii) said DEP electrodes comprise a photoconductive layer; or
(iii) said DEP electrodes comprise phototransistors.

13. The micro-fluidic device of claim 12, wherein said DEP electrodes are optically controlled.

14. The micro-fluidic device of claim 1, further comprising an electrode mechanism comprising an electrowetting device for moving a droplet of a first or second liquid medium in which one or more of said micro-objects are suspended.

15. The micro-fluidic device of claim 1, wherein said micro-fluidic device comprises a plurality of said channels, wherein each channel of said plurality is fluidically connected with a plurality of said holding pens.

16. The micro-fluidic device of claim 1, wherein all or part of said housing is gas permeable.

17. The micro-fluidic device of claim 1, wherein said housing comprises a flexible material.

18. The micro-fluidic device of claim 11, wherein said sensors detect the temperature, chemical composition, pH, or osmolarity of media within said chamber.

19. The micro-fluidic device of claim 1 further comprising an electrode mechanism comprising:
a first electrode;
a second electrode; and
an electrode activation substrate,
wherein said first electrode is part of a first wall defining said chamber, and wherein said second electrode and said electrode activation substrate are part of a second wall defining said chamber.

20. The micro-fluidic device of claim 19, wherein said electrode activation substrate is a photoconductive material.

21. The micro-fluidic device of claim 20, wherein said electrode activation substrate has a featureless surface.

22. The micro-fluidic device of claim 20, wherein said photoconductive material is undoped amorphous silicon.

23. The micro-fluidic device of claim 19, wherein said electrode activation substrate comprises a semiconductor material comprising a plurality of doped layers, electrically insulating layers, and electrically conductive layers that form semiconductor integrated circuits.

24. The micro-fluidic device of claim 19, wherein said electrode activation substrate comprises phototransistors.

25. A method of processing biological micro-objects, said method comprising:
actively placing individual biological micro-objects in interior spaces of holding pens in a micro-fluidic device according to claim 1;
providing to said holding pens a flow of a first liquid medium over a time period; and
while providing said flow, impeding direct flow of said first liquid medium from said flow into said interior spaces of said holding pens.

26. The method of claim 25, wherein said impeding comprises allowing diffusive mixing of said first liquid medium from said flow with second liquid medium in said interior spaces of said holding pens.

27. The method of claim 25 further comprising monitoring during said time period a characteristic of said micro-objects in said holding pens.

28. The method of claim 27, wherein said characteristic is a biological activity of said micro-objects in said holding pens.

29. The method of claim 28, wherein:
said biological activity comprises cloning, and
said monitoring comprises monitoring said cloning of said micro-objects in said holding pens.

30. The method of claim 28, wherein:
said biological activity comprises secreting secretions, and
said monitoring comprises monitoring said secretions of said micro-objects in said holding pens.

31. The method of claim 27, wherein said characteristic is a biological state of said micro-objects in said holding pens.

32. The method of claim 25, wherein said first liquid medium is a different type of medium than said second liquid medium.

33. The method of claim 25, wherein said first liquid medium is a same type of medium as said second liquid medium.

34. The method of claim 25 further comprising selecting from a plurality of said micro-objects in said micro-fluidic device a sub-set of said micro-objects that have a predetermined characteristic, wherein said actively placing comprises placing only said selected subset of said micro-objects in said holding pens.

35. The method of claim 34, wherein:
said plurality of micro-objects are in a common location in said micro-fluidic device,
said selecting comprises selecting each one of said micro-objects in said selected sub-set in said common location, and
said actively placing comprises moving each one of said micro-objects in said selected sub-set individually from said common location into one of said holding pens.

36. The method of claim 25, wherein said actively placing comprises placing one and only one of said individual micro-objects in each of said holding pens.

37. The method of claim 25, wherein said actively placing comprises activating dielectrophoresis (DEP) electrodes that create DEP forces on said individual micro-objects.

38. The method of claim 37, wherein said activating DEP electrodes comprises activating said DEP electrodes with an optoelectronic tweezers device.

39. The method of claim 25, wherein said providing comprises flowing said first liquid medium by openings in said holding pens.

40. The method of claim 25 further comprising maintaining said individual micro-objects in said holding pens during said time period.

41. The method of claim 25, wherein said placing comprises placing each of a plurality of different types of said micro-objects in each of a plurality of different interior spaces in one of said holding pens.

* * * * *

UNITED STATES PATENT AND TRADEMARK OFFICE
CERTIFICATE OF CORRECTION

PATENT NO. : 9,857,333 B2
APPLICATION NO. : 14/060117
DATED : January 2, 2018
INVENTOR(S) : Kevin T. Chapman et al.

Page 1 of 1

It is certified that error appears in the above-identified patent and that said Letters Patent is hereby corrected as shown below:

In the Claims

In Column 19, Line 47, please delete "holding" and replace with --holding pen--.

Signed and Sealed this
Twenty-sixth Day of June, 2018

Andrei Iancu
*Director of the United States Patent and Trademark Office*